US012797527B2

(12) United States Patent
Tsoory et al.

(10) Patent No.: US 12,797,527 B2
(45) Date of Patent: Nov. 17, 2026

(54) PUMP DEVICE, AND PERITONEAL DIALYSIS DEVICE, SYSTEM AND METHOD

(71) Applicant: LIBERDI LTD, Or Aqiva (IL)

(72) Inventors: Hezkiah Tsoory, Or Aqiva (IL); Dimitry Zacharin, Nesher (IL)

(73) Assignee: LIBERDI LTD., Or Aqiva (IL)

( * ) Notice: Subject to any disclaimer, the term of this patent is extended or adjusted under 35 U.S.C. 154(b) by 302 days.

(21) Appl. No.: 18/836,333

(22) PCT Filed: Feb. 5, 2023

(86) PCT No.: PCT/IB2023/051015
§ 371 (c)(1),
(2) Date: Aug. 6, 2024

(87) PCT Pub. No.: WO2023/148688
PCT Pub. Date: Aug. 10, 2023

(65) Prior Publication Data
US 2025/0144278 A1 May 8, 2025

(30) Foreign Application Priority Data
Feb. 6, 2022 (IL) .......................................... 290396
Nov. 13, 2022 (IL) .......................................... 298182

(51) Int. Cl.
*A61M 1/28* (2006.01)
*A61M 39/10* (2006.01)

(52) U.S. Cl.
CPC ............ *A61M 1/282* (2014.02); *A61M 1/285* (2013.01); *A61M 39/10* (2013.01)

(58) Field of Classification Search
CPC ...... A61M 1/1524; A61M 1/152; A61M 1/15; A61M 1/1565; A61M 1/159; A61M 1/28
See application file for complete search history.

(56) References Cited

U.S. PATENT DOCUMENTS 2,693,765 A 11/1954 Evert
8,330,579 B2 * 12/2012 Kneip .................. A61M 1/152
604/29

(Continued)

FOREIGN PATENT DOCUMENTS

DE 102014207238 A1 10/2015
EP 0026704 A1 4/1981

(Continued)

OTHER PUBLICATIONS

Extended European Search Report for European Patent Application No. 23749417.4, Jan. 16, 2026, 05 pages.

(Continued)

*Primary Examiner* — William R Carpenter
(74) *Attorney, Agent, or Firm* — RECHES PATENTS

(57) ABSTRACT

Embodiments pertain to a peritoneal dialysis system, comprising: a controller; a durable unit, and a disposable unit that comprises a housing and that is removably couplable with the durable unit, the disposable unit configured to receive a tube having a channel, the tube being compressible by a wheel of the pump such to cause flow of fluid within the channel. The disposable unit and/or the tube comprises at least one flow breaker configured to block the fluid of fluid through the tubing. The durable unit further comprises a slider platform for receiving at least one biasing element; and at least one actuator controllable by the controller. The slider platform can be actuated to controllably slide, relative to the at least one flow breaker, from a retracted position to an advanced position for changing a flow breaker configuration.

20 Claims, 29 Drawing Sheets

(56) References Cited

U.S. PATENT DOCUMENTS

| | | | | |
|---|---|---|---|---|
| 8,764,702 | B2 * | 7/2014 | Childers | A61M 1/1522 604/533 |
| 10,754,002 | B1 | 8/2020 | Gibbons | |
| 2011/0106002 | A1 * | 5/2011 | Helmore | A61M 1/1565 604/533 |
| 2017/0112992 | A1 | 4/2017 | Plahey et al. | |
| 2019/0145398 | A1 | 5/2019 | Nagahama et al. | |
| 2019/0145399 | A1 | 5/2019 | Hayashi | |
| 2019/0316948 | A1 | 10/2019 | Karol et al. | |
| 2019/0381231 | A1 | 12/2019 | Tsoory et al. | |

FOREIGN PATENT DOCUMENTS

| | | | | |
|---|---|---|---|---|
| EP | 3558444 | A1 | 10/2019 | |
| WO | WO-2017134657 | A1 * | 8/2017 | A61L 2/18 |

OTHER PUBLICATIONS

International Preliminary Report on Patentability for Application No. PCT/IB2023/051015, mailed on Aug. 15, 2024, 07 pages.

International Search Report and Written Opinion from International Application No. PCT/IB2023/051015 mailed May 16, 2023, 12 pages.

Israel Office Action for Patent Application No. 290396 dated May 22, 2022, 9 pages—English Translation Available.

P10884-IL1_298182_OA1 mailed Feb. 26, 2023.

* cited by examiner

PUMP DEVICE, AND PERITONEAL DIALYSIS DEVICE, SYSTEM AND METHOD

CROSS-REFERENCE TO RELATED APPLICATIONS

This application claims priority of IL patent application No. 290396 filed on Feb. 6, 2022, titled "PUMP DEVICE, AND PERITONEAL DIALYSIS DEVICE, SYSTEM AND METHOD"; and of IL patent application No. 298182 filed on Nov. 13, 2022, titled "PUMP DEVICE, AND PERITONEAL DIALYSIS DEVICE, SYSTEM AND METHOD". The contents of the above applications are all incorporated by reference as if fully set forth herein in their entirety

FIELD OF THE INVENTION

The present invention, in some embodiments thereof, relates to a systems, devices and methods for dialysis treatment.

BACKGROUND

Peritoneal Dialysis is a lifesaving procedure for removing waste and excess water from the blood. It is used primarily to sustain the health of patients who have experienced renal failure.

The peritoneal dialysis removes wastes and excess water from the blood inside the body using the peritoneum as a natural semipermeable membrane. Wastes and excess water move from the blood, across the peritoneal membrane, and into a special dialysis solution, called dialysate, in the abdominal cavity and more specifically the peritoneal cavity. The waste materials that are removed include uremic wastes, excess water, and excess minerals.

BRIEF DESCRIPTION OF THE DRAWINGS

The figures illustrate generally, by way of example, but not by way of limitation, various embodiments discussed in the present document.

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. References to previously presented elements are implied without necessarily further citing the drawing or description in which they appear. The figures are listed below.

DETAILED DESCRIPTION

The principles and operation of an improved peritoneal dialysis device according to the present invention may be better understood with reference to the drawings and the accompanying description.

Figure 1:
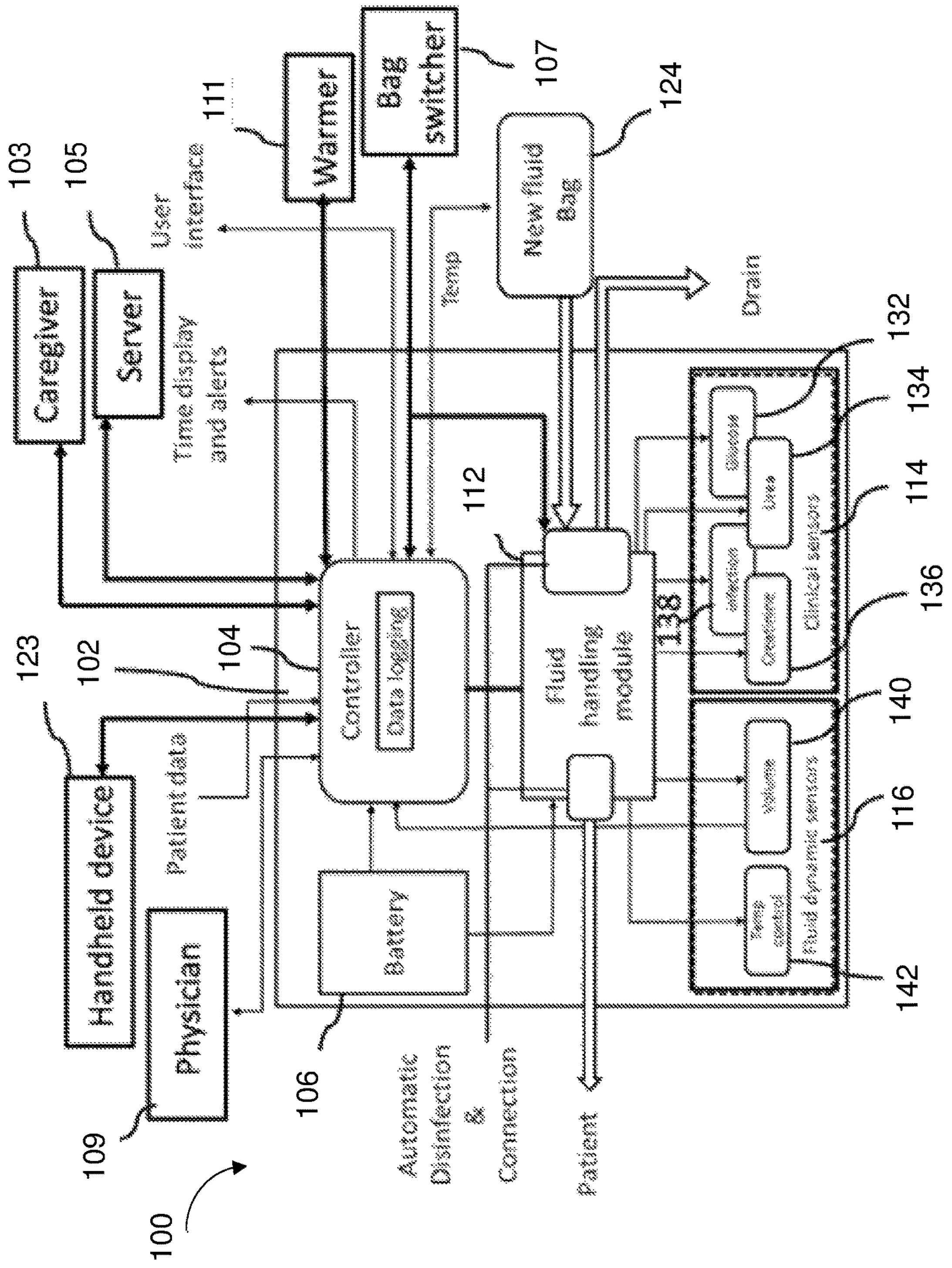
FIG. 1 is a schematic block diagram of a dialysis system, according to some embodiments.

Referring now to the drawings, FIG. 1 illustrates a system or a device for a peritoneal dialysis treatment, according to some embodiments.

According to some embodiments, dialysis system 100 comprises a dialysis device 102, a dialysate bag 124 or a draining bag, and a patient catheter connectable to a patient 130. In some embodiments, dialysis device 102 is connectable to dialysate bag 124 and/or to the draining bag, and optionally to form a disinfected flow path between the bags and the patient 130, through the release of disinfection material stored in the tubing.

According to some embodiments, dialysis device 102 comprises a controller 104 and a fluid handling module 112, which comprises a pump. In some embodiments, controller 104 controls the operation of the fluid handling module, for example when the fluid handling module is activated to infuse dialysate into the peritoneal cavity, or when the fluid handling module is activated to drain the peritoneal cavity.

In some embodiments, the controller 104 controls the connection of the dialysate bag 124 and/or the draining bag to dialysis device 102. Additionally, in some examples, controller 104 controls the connection of a patient catheter to dialysis device 102.

According to some embodiments, controller 104 monitors and controls the automatic connection and disinfection of different components connected to the flow path.

In some embodiments, the controller delivers an indication, for example a human detectable indication, when a component is connected to the flow path and/or when the flow path is disinfected. Alternatively, or additionally, the controller stores the indication in a memory.

According to some embodiments, the controller 104 monitors the flow within the flow path by different sensors of dialysis device 102, for example fluid dynamic sensors 116. In some embodiments, the fluid dynamic sensors comprise at least one volume sensor 140, for example for monitoring the volume of fluid padding through the flow path. Additionally, the fluid dynamic sensors comprise at least one temperature control sensor 142, for example, for monitoring and controlling the temperature of fluid passing through the flow path.

According to some embodiments, dialysis device 102 comprises at least one clinical sensor 114 for example for sensing changes in clinical parameters. In some embodiments, the at least one clinical sensor senses the chemical and/or biological content of the drained dialysate, for example using a creatinine sensor 136, and/or a urea sensor 134 and/or glucose sensor 132. Optionally, one or more biosensors 138 can sense several biomolecules, for the detection of relevant clinical pathogens such as bacteria and viruses. Optionally, the dextrose/glucose sensor 132 senses the dextrose/glucose levels in the infused dialysate.

According to some embodiments, dialysis device 102 comprises at least one glucose/dextrose sensor 132 configured to measure glucose/dextrose levels in the drained dialysate. According to some embodiments, dialysis device 102 comprises at least one sensor for detection of Urea levels, for example Urea sensor 134. In some embodiments, dialysis device 102 comprises at least one sensor for detection of creatinine levels in the dialysate, for example a creatinine sensor 136. In some embodiments, the levels of creatinine in the drained dialysate optionally, compared to the creatinine levels in the fresh dialysate, are indicative of the clinical condition of the subject. In some embodiments, the clinical sensors 114 are activated during a treatment session, for example during the infusion and/or draining of the dialysate.

According to some embodiments, the controller delivers indications and/or alerts to a patient or to a caregiver in the vicinity of dialysis device 102. Alternatively, or additionally, the controller transmits indications and alerts to a remote computer, for example a computer of a physician. In some embodiments, the physician transmits information to dialysis device 102, for example to modify at least one treatment parameter or to select a different treatment plan.

According to some embodiments, dialysis device 102 delivers time reminders to a patient and/or indications to perform a treatment step. In some embodiments, the user of the device, for example the patient or a caregiver, provides user input through a user interface, which is optionally comprises at least one button, for example an activation or a treatment termination button.

In some embodiments, the input received from the user and additional user data are stored in dialysis device 102. In some embodiments, the stored user data is transmitted to a physician, for example to allow remote monitoring of the user condition throughout the treatment process. In some examples, dialysis device 102 activation log files are also stored, and are optionally used to generate a patient compliance report following a treatment session. According to some embodiments, dialysis device 102 further comprising a power unit (e.g., battery, a connection to an external power source) 106, for powering the various components of the dialysis device, e.g., to allow the activation of the controller 104 and/or an electric pump optionally connected to the fluid handling module 112. In some examples, the battery is electrically connected to an electric motor optionally connected to the fluid handling module 112.

In some embodiments, dialysis device 102 comprises a charging socket or plug electrically connected to the battery, for example to allow electrical charging of the battery by an external power source. Alternatively, the battery is a replaceable battery. In some embodiments, the control unit controls the activation of the motor according to the power level in the battery.

In some embodiments, the durable unit comprises an interface connected to the control circuitry, configured to provide at least one human detectable indication, for example an alert signal by a light indication and/or a sound indication. The durable unit may comprise a case.

In some embodiments, when the power level in the battery is lower than a low threshold value, then the control circuitry signals the interface to generate an alert signal, for example a signal indicating to charge the battery or to replace the battery. Alternatively, or additionally, when the power level in the battery is lower than a low-threshold value, the control circuitry stops the operation of the motor.

According to some embodiments, the control circuitry activates the motor in a power saving mode, for example when the power level in the battery is lower than a power threshold value. The threshold may be a dynamic threshold, or an adaptive threshold or a predetermined threshold.

In some embodiments, the control circuitry modifies at least one activation parameter value of the motor, for example rotation speed and/or rotation duration, optionally when activating the motor in a power saving mode. In some embodiments, the control circuitry prevents the activation of the motor when the battery power level is lower than a low-threshold value.

According to some embodiments, the power level in the battery when the battery is fully charged is sufficient for at least one dialysis treatment session, for example 2 treatment sessions, 3 treatment sessions, 4 treatment sessions or any smaller, intermediate or larger number of treatment sessions.

In some embodiments, a treatment session includes at least partly draining of dialysate from the peritoneal cavity and at least partly infusion of fresh dialysate into the peritoneal cavity. In some examples, a treatment session includes at least partly draining of dialysate from the peritoneal cavity, at least partly infusion of fresh dialysate into the peritoneal cavity and the dwelling time of the dialysate within the peritoneal cavity.

According to some embodiments, dialysis device 102 is connected to a computer server, for example server 105. In some embodiments server 105 stores treatment protocols and/or device activation log files. In some embodiments, controller 104 writes into server 105 measured values of parameters related to the device operation and/or parameters related to the clinical condition of the patient. Optionally, a physician communicates with the server 105, for example to receive log files of the device and/or to deliver treatment instructions or modifications. In some embodiments, the server 105 transmits information to a caregiver, for example a nurse or a warehouse, for example to supply new dialysate bags.

According to some embodiments, dialysis device 102 communicates with a caregiver 103, for example to provide the caregiver clinical information of the patient and/or other information related to the treatment. In some embodiments, dialysis device 102 communicates with a physician 109. In some embodiments, dialysis device 102 delivers alerts to the physician 109 if actual treatment is different from a pre-determined treatment. Alternatively, or additionally, dialysis device 102 delivers alerts to the physician 109, if a desired outcome of the treatment is not reached. In some embodiments, the physician 109 communicates with the patient through dialysis device 102, for example to deliver instructions and/or to receive more information from the patient.

According to some embodiments, dialysis device 102 is connected to or comprises a bag switcher 107. In some embodiments, dialysis device 102, optionally a detachable and/or portable device is attached to the bag switcher 107 during a peritoneal dialysis treatment, for example an exchange process. In some embodiments, at least one dialysate bag, for example bag 124 is connected to the bag switcher 107. In some embodiments, the bag switcher 107 validates that the correct bag is connected, optionally using a barcode or a different ID of the bag. In some embodiments, the bag switcher 107 monitors the temperature of the bag, and optionally heats the bag using a heating mechanism. In some embodiments, when the exchange session is over the detachable device is disconnected from the bag switcher 107. According to some embodiments, the device comprises a warmer, for example warmer 111. Alternatively, the warmer is part of dialysis system 100 and/or is part of bag switcher 107. In some embodiments, the warmer is used to monitor and/or control the temperature of the dialysate bags.

In some embodiments, the controller 104 receives signals from the warmer 111 or from a temperature sensor regarding the temperature of the dialysate. In some embodiments, the controller 104 signals the warmer 111 to heat the dialysate fluid, for example by heating the dialysate bag. Alternatively, the controller 104 signals the bag switcher 107 to switch the dialysate bag to a bag with a desired dialysate temperature.

According to some embodiments, dialysis device 102 communicates with a handheld device 123, for example a cellular phone. In some embodiments, dialysis device 102 transmits alerts and/or indications and/or information to the handheld device 123. Optionally, dialysis device 102 communicates with the handheld device 123 using an application program installed in the device. In some embodiments, dialysis device 102 delivers time alerts prior to initiation of a treatment or any time alert to the handheld device 123. In some embodiments, the handheld device controls at least partially the activation of dialysis device 102, optionally using the application program. In some embodiments, dialysis device 102 receives information from devices connected to the handheld device 123, for example a smart watch or any other wearable sensor.

Example Device Interactions and Functions

Figure 2:
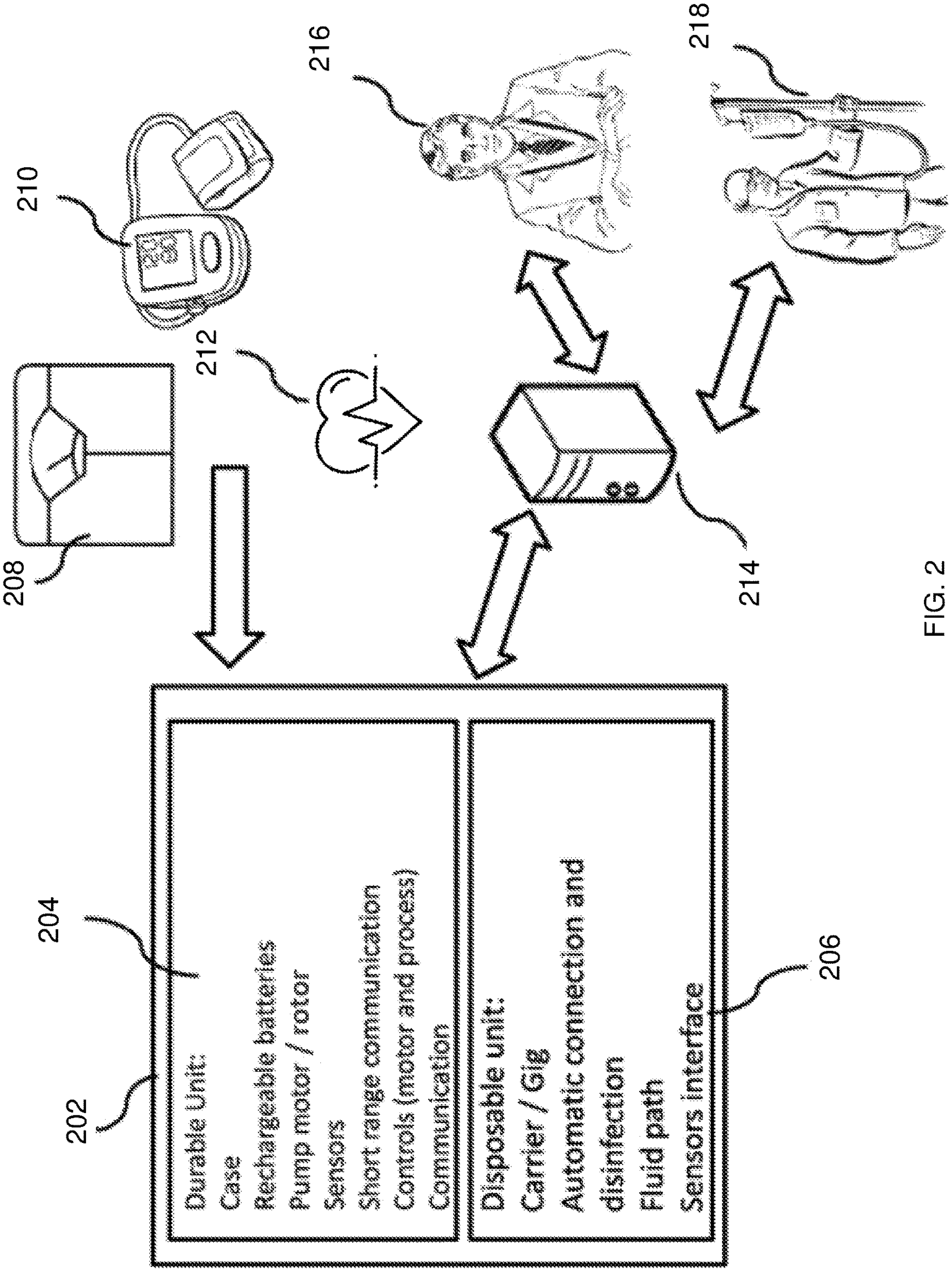
FIG. 2 is a schematic illustration of the dialysis system, according to some embodiments.

Reference is now made to FIG. 2 depicting interactions and functions of the peritoneal dialysis device, according to some embodiments.

According to some embodiments, a portable peritoneal (PP) dialysis device 202 comprises a PP Dialysis Machine, for example durable/reusable unit 204 and a PP disposable unit 206. In some embodiments, the durable unit 204 comprises a case, a power unit for example a battery, a pump motor, for example an electrical pump motor, and a pump rotor. In some embodiments, the durable unit further comprises at least one sensor, a communication module and, e.g., a controller, for example, to control the dialysis treatment process and motor and/or for controlling operation of a sliding platform. In some embodiments, different controllers or a same controller may be employed for controlling the sliding platform and/or the dialysis process. In some embodiments, a controller may be external to the durable unit.

According to some embodiments, the disposable unit 206 comprises a carrier, a connection module, optionally an automatic connection module. In some embodiments the connection module is also a disinfection module. In some embodiments, the disposable unit 206 comprises at least one sensor, for example a clinical sensor for measuring clinical parameters of the treatment and/or clinical parameters of the patient connected to a dialysis device 202.

According to some embodiments, a dialysis system 300 comprising dialysis device 202 measures clinical parameters of the patient, for example body weight 208, blood pressure 210 and/or heart rate 212. In some embodiments, dialysis system 300 writes the measured parameter values and other information on a memory of the system or in a remote memory 214. In some embodiments, dialysis system 300 reads from remote memory 214 treatment plans and treatment parameters. Additionally, the device transmits the stored information to a physician 216 and/or to the patient 218. In some embodiments, the physician 216 transmits information, for example suggested treatment protocol or suggested protocol modifications to the remote memory 214 or directly to a memory of dialysis system 300.

Figure 3:
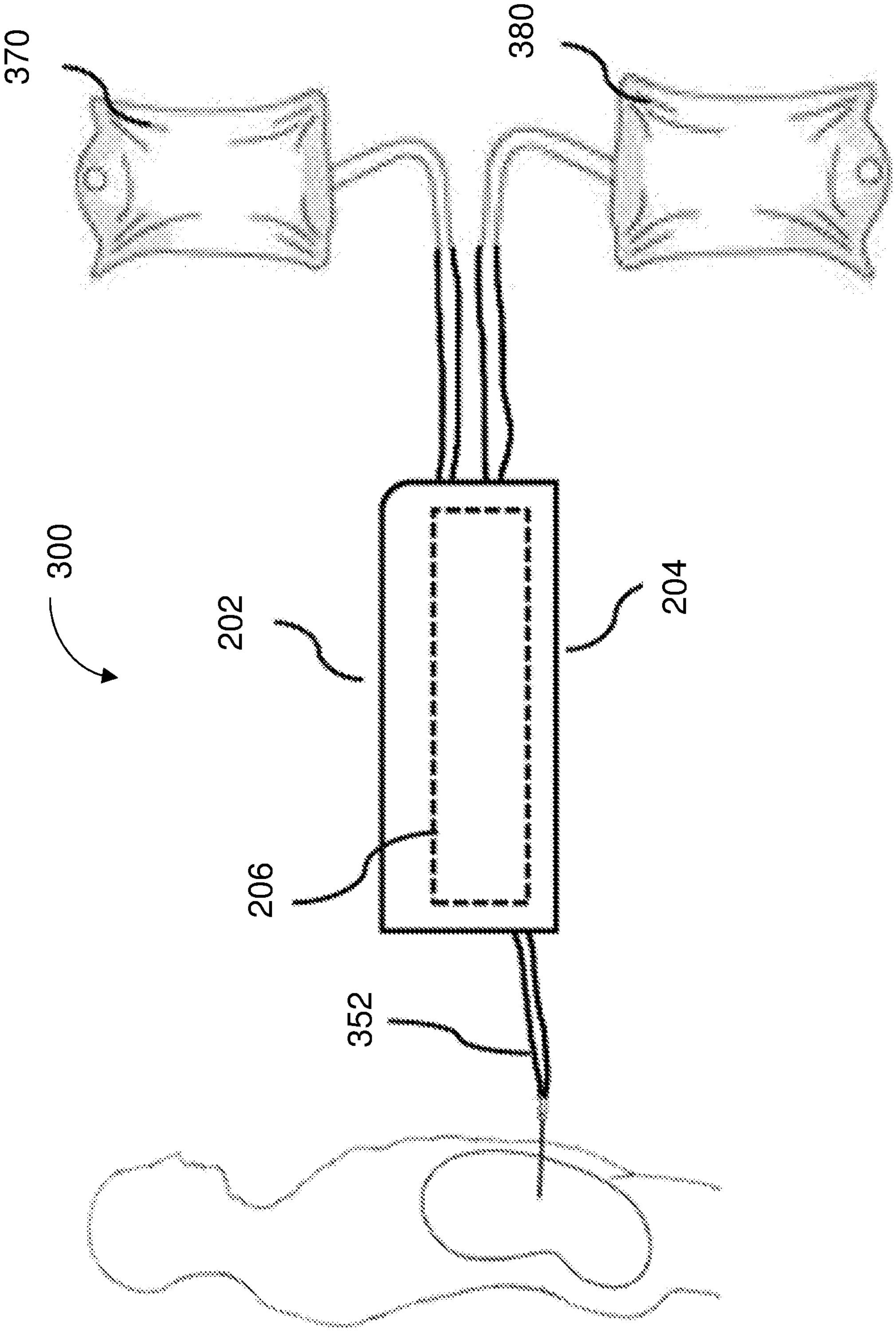
FIG. 3 is a schematic illustration of a dialysis device fluidly coupled with a patient, a fresh dialysate bag and a used dialysate bag, according to some embodiments.

Reference is made to FIG. 3, depicting a system for delivery of a peritoneal dialysis treatment, according to some embodiments.

According to some embodiments, a Portable Peritoneal (PP) Dialysis System, for example dialysis system 300 comprises at least one bag, for example a fresh dialysate bag 370 and a drained dialysate bag 380, connected to a connector of system 300. In some embodiments, a patient catheter tube 352 is connected to a different connector of system 300.

Figure 4:
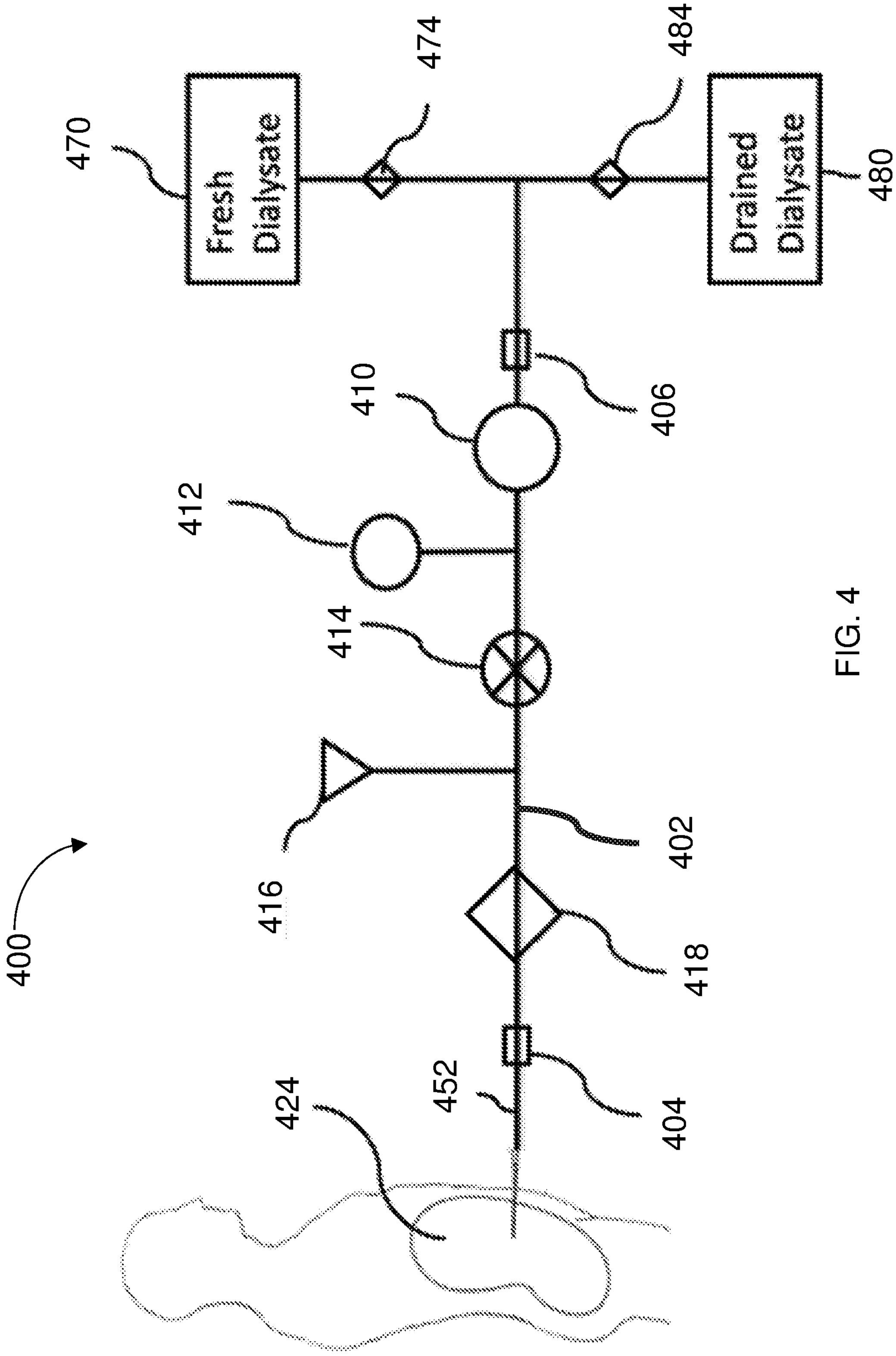
FIG. 4 is as schematic piping and instrumentation diagram of dialysis system, according to some embodiments.

Reference is made to FIG. 4 depicting a system 400 for monitoring and/or controlling a peritoneal dialysis treatment, according to some embodiments.

According to some embodiments, a new dialysate solution storage compartment 470 is connected via a flow breaker 474 to a connector 406, for example a y-connector. In some embodiments, a used dialysate storage compartment 480 is connected via a flow breaker 484 to the connector 406. In some embodiments, flow breakers 474 and 484 are used to close the flow path between the storage compartments and the connector 406. In some embodiments, the connector 406 automatically, semi-automatically or under manual manipulation disinfects the flow path towards each of the compartments.

As outlined herein in more detail, a flow breaker may in some embodiments be implemented as a valve, a diaphragm, a mechanical energy storage device, and/or the like.

According to some embodiments, the connector 406 is positioned in the distal end of pump tubing, which is associated with a rotor of a peristaltic pump 410. In some embodiments, at least one pressure sensor, for example pressure sensor 412 senses the pressure of the fluid within the pump tubing. In some embodiments, at least one flow sensor, for example flow sensor 414 senses the flow speed and/or the fluid volume within the pump tubing. In some embodiments, at least one peritonitis sensor, for example peritonitis sensor 416 senses the formation of peritonitis within the peritoneal cavity, as previously described. In some embodiments, the fluid within the pump tubing passes through a heating unit 418. In some embodiments, heating unit 418 heats the fresh dialysate fluid within the pump tubing to a desired temperature, before it is infused into the patient's catheter.

According to some embodiments, a patient catheter 452 connects the peritoneal cavity 424 of a patient via a connector 404. In some embodiments, the connector 404 is connected to the proximal end of the pump tubing 402. In some embodiments, the connector 404 automatically or semi-automatically connects the patient catheter to the proximal end of the pump tubing. Additionally, or optionally, the connector 404 automatically or semi-automatically causes or facilitates disinfection of a flow path between the patient's catheter and the pump tubing.

Additional reference is made to FIG. 5A to 5E. Disposable unit 500 may be a type of cartridge that is removably coupleable with a durable unit 600 having a base part 602 and a lid 610 for selectively opening and closing the base part 602.

In some examples, base part 602 may comprise the pump including pump rotor 700. In some examples, cartridge 500 may comprise part of pump rotor 700.

In some embodiments, disposable unit 500 may be removably coupled with a cartridge receiving rack of a durable unit.

For example, lid 610 may be configured as or comprise a cartridge receiving rack, and disposable unit 500 may be removably coupled with (e.g., inserted into) the lid section 610 of the durable unit 600. Closing the lid 610 may bring the disposable unit 500 in operable engagement with the pump.

In some other embodiments, the disposable unit 500 may be placed unto or otherwise be brought in operable engagement with the pump. For example, the disposable unit 500 may be placed unto or otherwise be brought in operable engagement with the pump (e.g., by placing the disposable unit 500 into a retractable drawer (not shown).

In some embodiments, the pump tubing interacts or operably engages with the pump, allowing the pump to displace fluid in the tube in a desired direction at a desired speed, e.g., peristaltically.

The tubing of the disposable unit is adapted to be (e.g., removably) coupled with the patient catheter on one end and with the dialysate bags on the other end. The pump controls the direction and speed of the fluids that are pumped (e.g., peristaltically) through the tubing.

In some embodiments, the tubing also includes a sterilizing fluid that at least partially or fully sterilizes the catheter (tubing and connector) and/or y-connector and/or tubing to the dialysate bags.

The disposable unit 500 is adapted to be discarded after a single use. The cartridge or disposable unit 500 is an example of an implementation of the disposable unit 206 shown in FIGS. 2 and 3, whereas the durable unit 600 is an example of an implementation of durable unit 204 shown in FIGS. 2 and 3.

When looking back at FIG. 4, some or all components between connector 406 and connector 404 can be implemented in the disposable unit 500 and the durable unit 600. In a non-limiting example, the connectors 404 and 406 along with tubing 402 may be found in the disposable unit, whereas the pump 410, sensors 412, 414 and 416 as well as the heating element 418 may be disposed in the durable unit.

According to some embodiments, disposable unit 500 comprises a pump tubing 502 having a catheter connector 504, and a (fresh and/or drained) dialysate Y-set tubing connector 506.

In some embodiments, a flow breaker, for example a mechanical energy storage element (e.g., a spring) or a blocking element, is positioned on the tubing 502, e.g., next to the connector, for example, as flow breakers 508A and 508B.

Flow breaker may comprise or may be operably coupled with an actuator and, optionally, a controller configured to set flow breaker from a closed (also: blocking) to an open (also: non-blocking) configuration, e.g., as described herein. Flow breaker may be automatically, semi-automatically or manually actuatable.

In some embodiments, the flow breaker may be biased to be in the closed (also: blocking) configuration, for example, by a mechanical storage element (e.g., a torsion spring).

In some embodiments, the flow breaker is biased to be in an open (also: non-blocking) configuration, for example, by a mechanical storage element (e.g., a torsion spring).

In some embodiments, the flow breaker is idle with respect to the open and closed configuration.

Figure 5B:
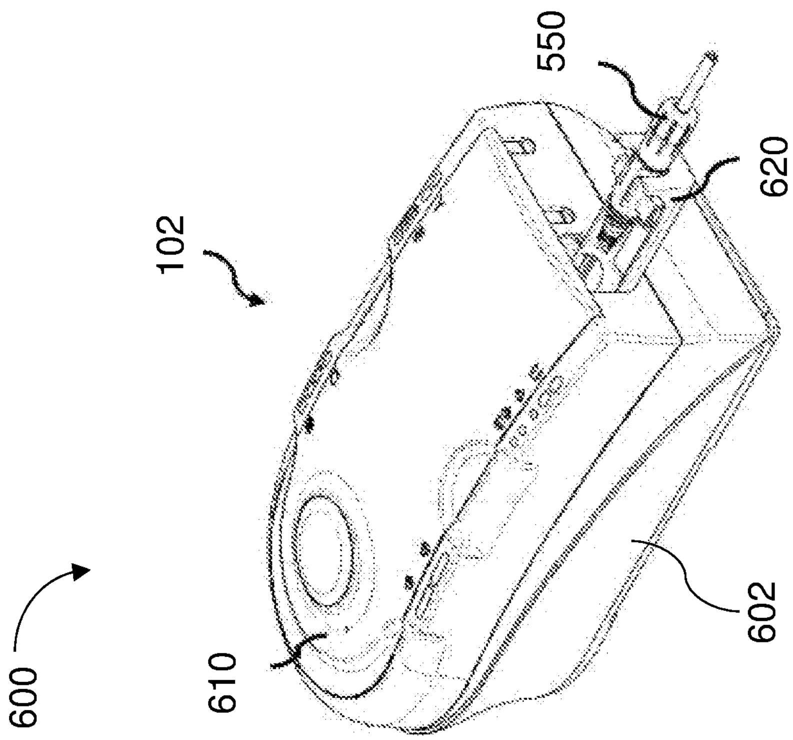
FIG. 5B is a schematic illustration of a dialysis device with its lid closed, according to some embodiments.
Figure 5A:
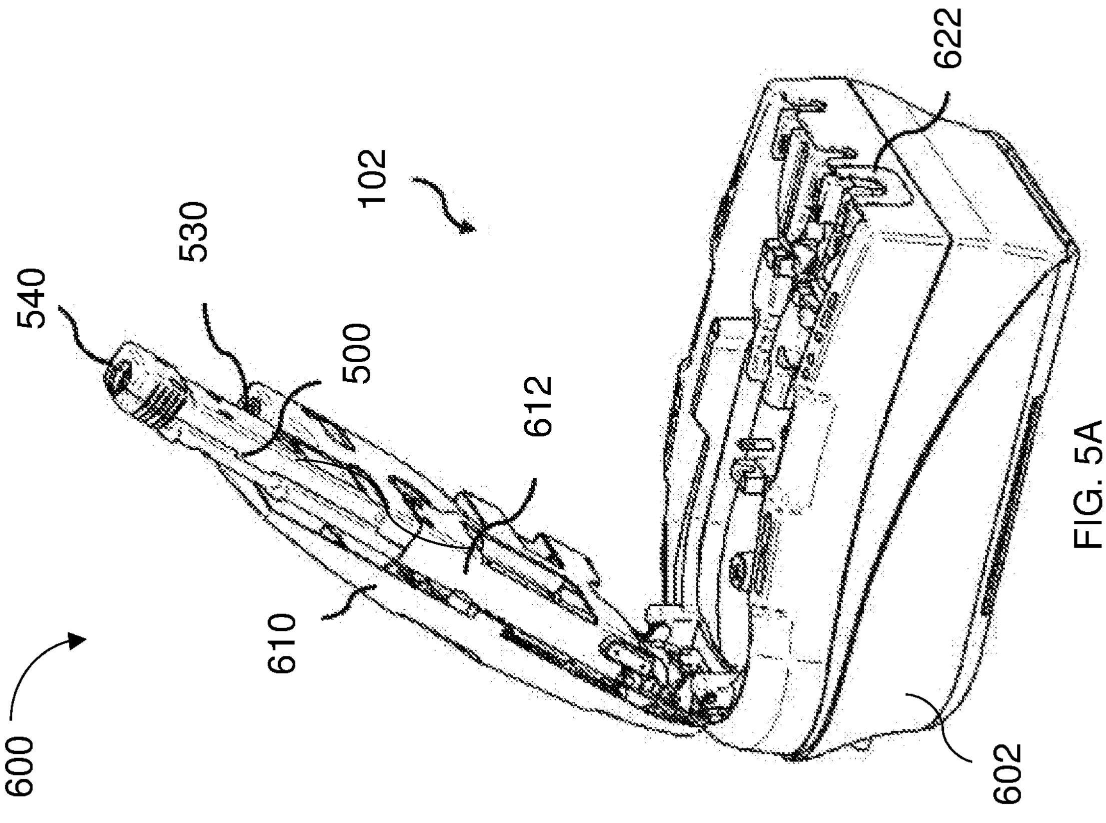
FIG. 5A is a schematic illustration of a dialysis device with its lid opened, according to some embodiments.
Figures 5C, 5D:
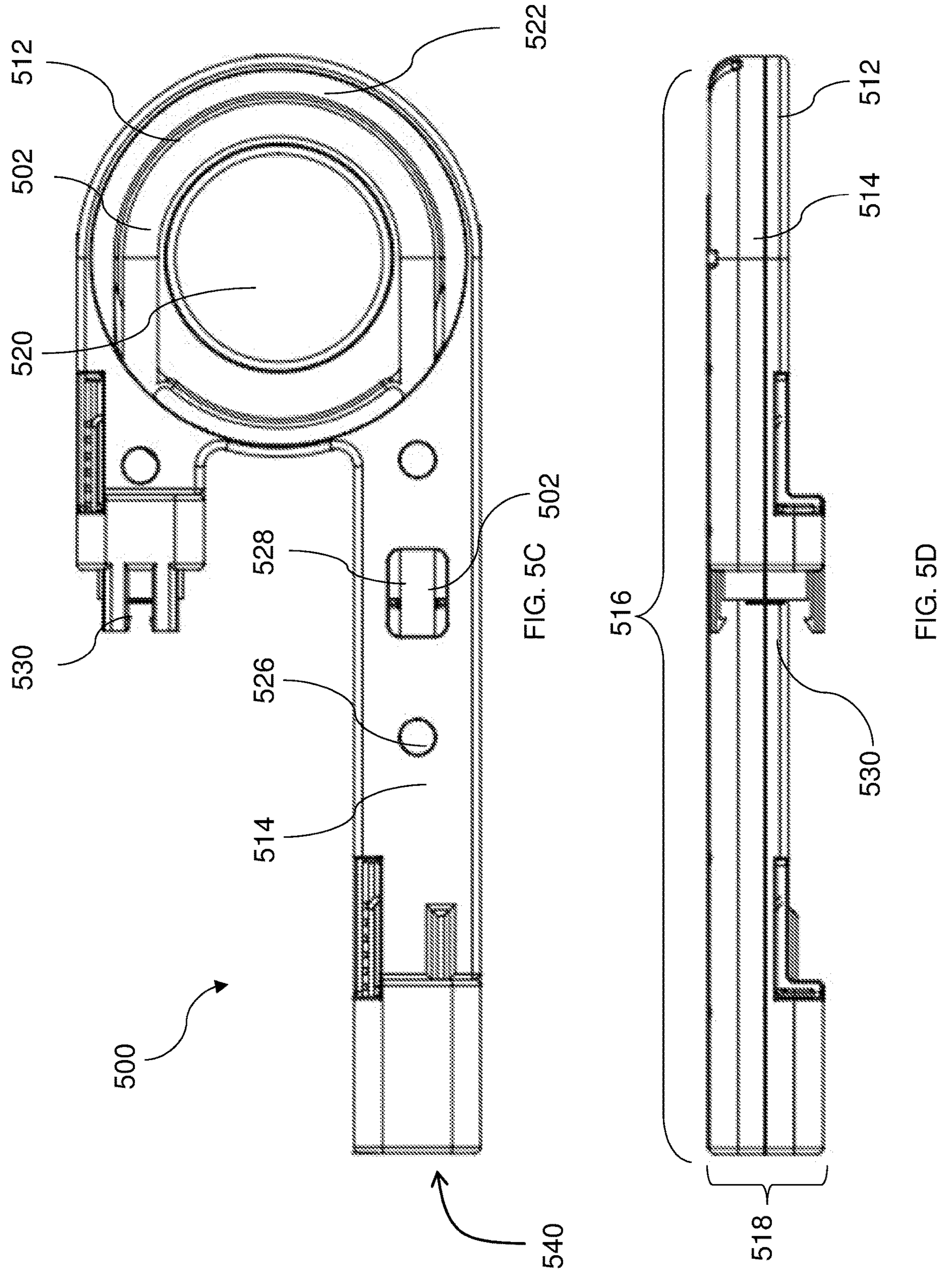
FIG. 5C is a schematic bottom view of a disposable cartridge of the dialysis device, according to some embodiments.
FIG. 5D is a schematic side view of the disposable cartridge of the dialysis device, according to some embodiments.
Figure 5E:
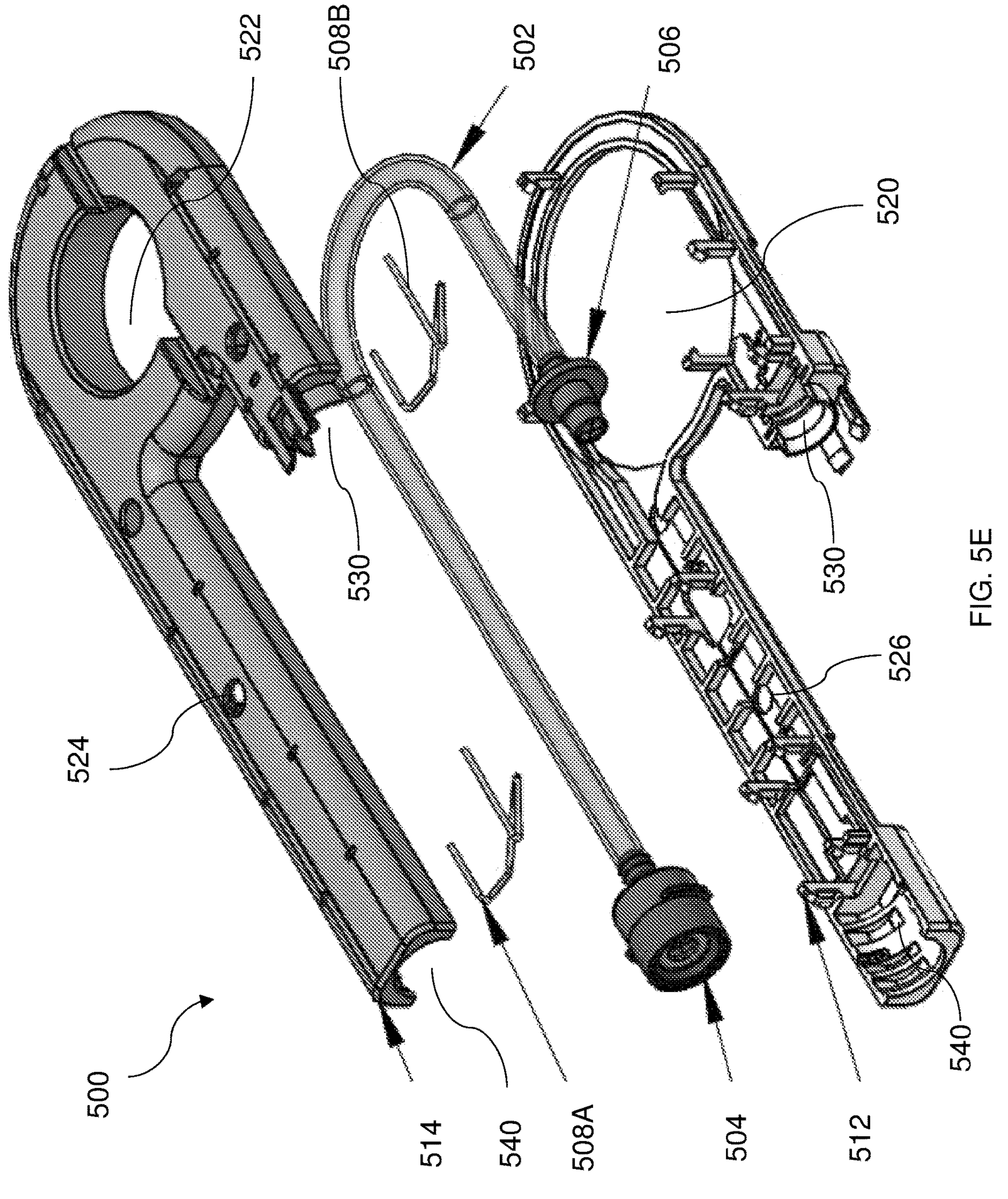
FIG. 5E is a schematic exploded view of the disposable cartridge, according to some embodiments.
Figure 5F:
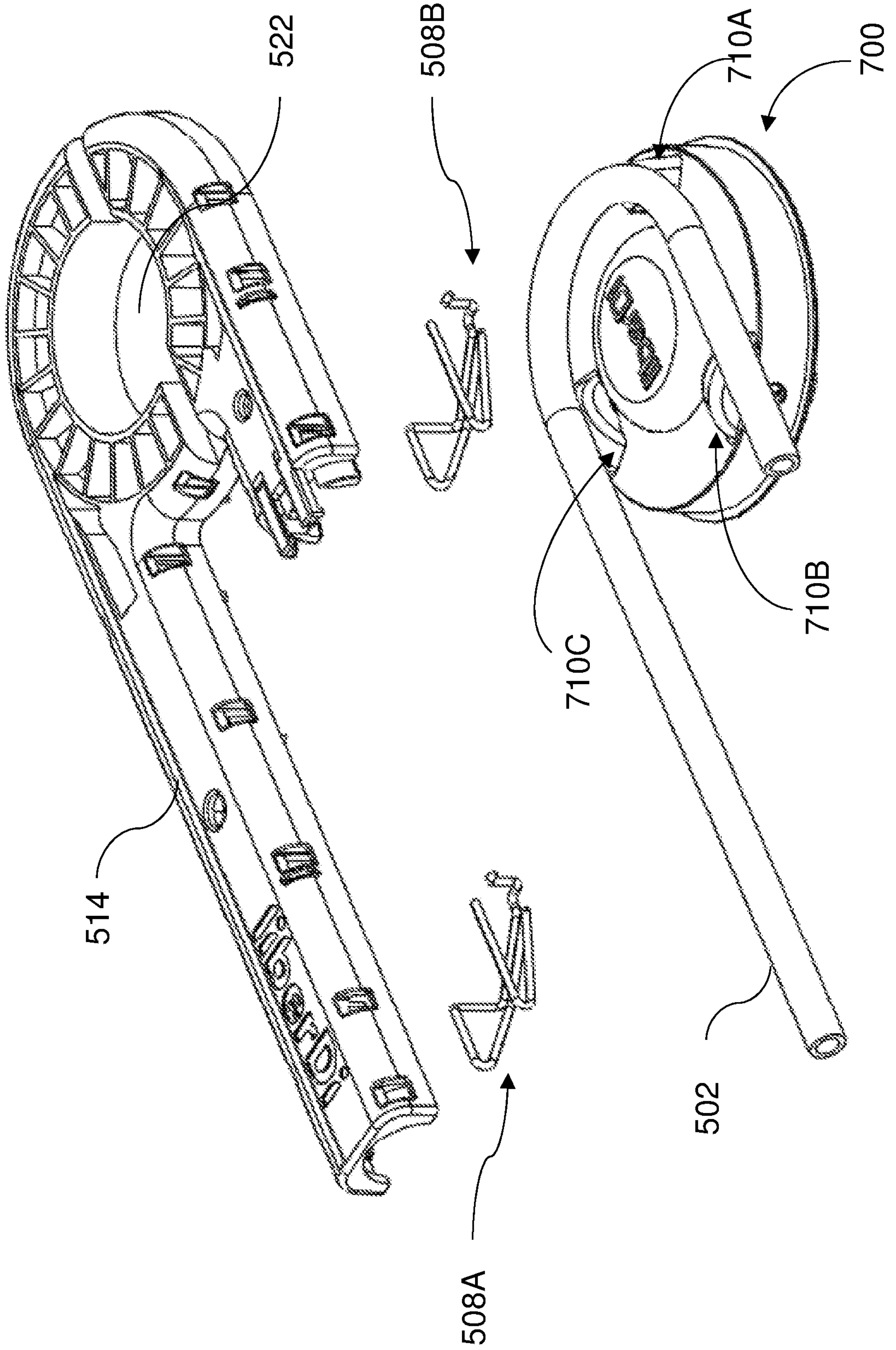
FIG. 5F is a schematic illustration of parts of the disposable cartridge and of a pump engaging with tubing of the dialysis system, according to some embodiments.
Figure 5G:
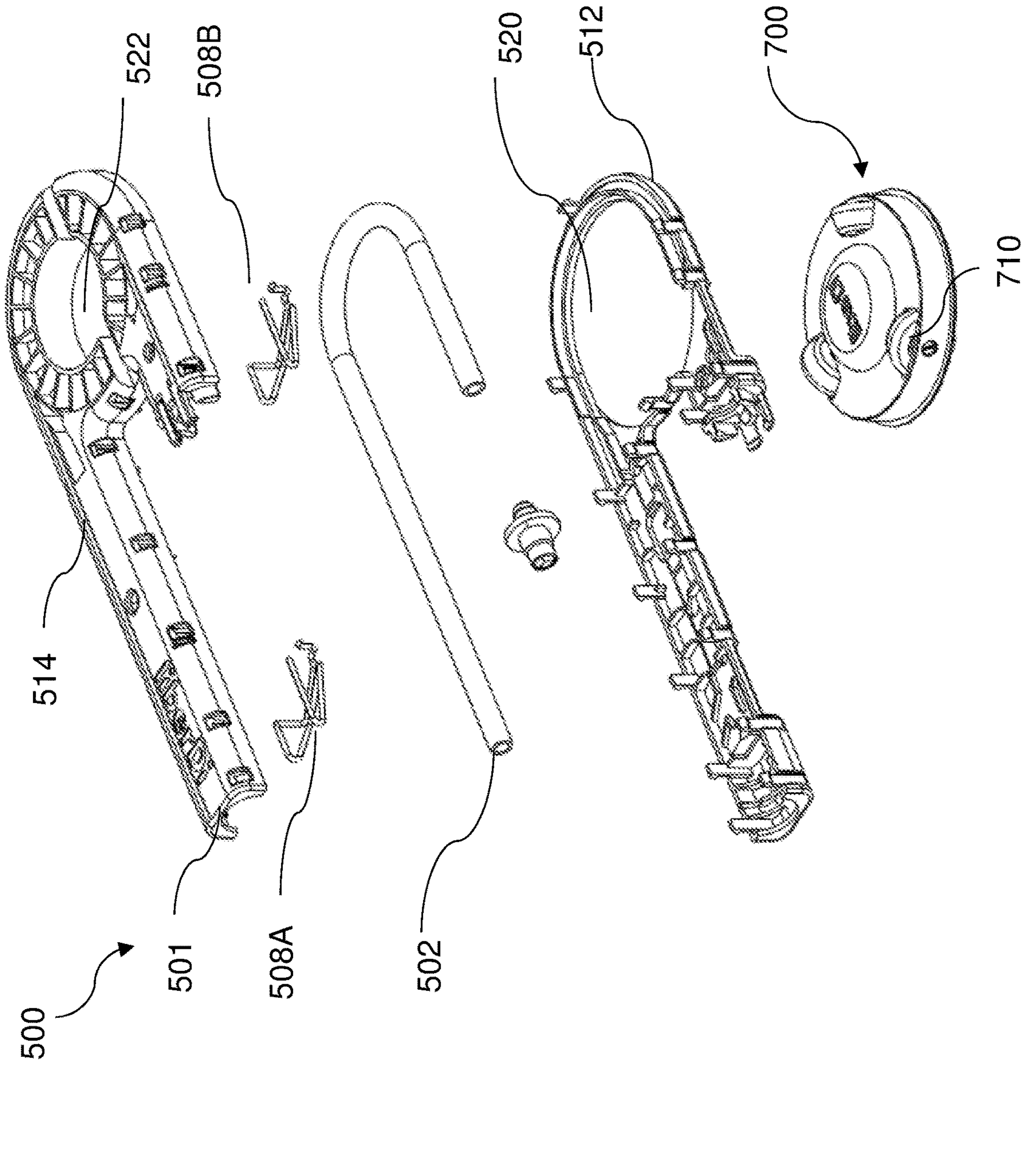
FIG. 5G is a schematic illustration of parts of the disposable cartridge and of the pump of the dialysis system, according to some embodiments.

Additional reference is made to FIGS. 5F and 5G. Disposable unit 500 may comprise a lower casing or base part 512 having a lower opening 520, and an upper casing or cover part 514 having an upper or cover opening 522, configured to operably receive pump rotor 700. When disposable unit 500 is assembled with durable unit 600, wheels or rollers 710 of pump rotor 700 operably engage with pump tubing 502 for peristaltically cause flow of fluid in tubing 502.

FIGS. 5E to 5G also illustrate a plurality of flow breakers, e.g., spring flow breakers 508A and 508B in a closed configuration, compressing tubing 502. Flow breaker 508B is shown to be positioned next to catheter connector 504 preventing fluid from entering or exiting the tubing 502.

In some embodiments, when the flow breakers are set in the closed configuration, fluid does not flow into and out from the pump tubing. In some embodiments fluid can flow into and out from the pump tubing only when the flow breakers are at least partly open. Each of flow breakers 508A and 508B has a closed state and an open state. In the closed state, the flow breaker (e.g., a uniquely designed spring) restricts flow within in the tubing. In the open state, flow within the tubing is unrestricted.

In some examples, a flow breaker may be configured to be "normally open", e.g., configured such that energy must be applied onto the flow breaker to cause blockage of the tubing. In some other examples, a flow breaker may be configured to be "normally closed", e.g., by default configured to apply blocking pressure onto the tubing, such that energy must be applied to retain the breaker in the open configuration.

In some embodiments, the flow breaker is a spring 800 (see below more details in FIGS. 8A to 8E). The spring has a resting position and a biased position. In the resting position (e.g., depicted in FIGS. 8A and 8B), the spring restricts flow to the tubing (e.g., as depicted in FIG. 5D). In the biased position (e.g., depicted in FIG. 8C), the spring allows flow, at least partially, in the tubing. More precisely, the spring has a biased condition (not a single biased position but rather a range of positions) whereby the spring, at least partially, allows fluid to flow in the tubing. The spring may be biased partially or fully allowing fluid to flow within the tubing at different rates.

In some examples, the resting position is the default position; therefore, the closed state is the default state. Accordingly, in embodiments where the flow breaker is implemented as spring 800, the flow breaker is considered normally closed.

In some examples, the spring goes from the closed state to the open state by biasing the spring from the resting position/condition to/into the biased position/condition. In some embodiments, the open state is achieved by laterally moving a biasing element that squeezes two angled apart sections of the spring together, biasing the spring into an open configuration. Moving the biasing element back to an initial position releases the angled apart sections, thereby unbiasing the spring and allowing it to return to its resting condition, in which tubing is compressed between two wire spring sections, e.g., as shown schematically in FIG. 8A.

According to other embodiments, the flow breaker has a closed state and an open state. The closed state is the initial state. The open state is achieved by breaking the flow breaker. In such embodiments, the flow breaker cannot be returned to the closed state. Moreover, such a flow breaker has a bi-stable, non-reversible, switch that moves the flow breaker from a closed state to an open state where it remains permanently.

In embodiments where the primary function of the flow breakers breaker is to release the sterilizing fluid at the appropriate time it may not be necessary for the flow breaker to return to the closed state once the sterilizing fluid has left the tubing. On the other hand, being able to return to the closed state may be necessary in embodiments where the flow breakers serve one or more additional functions, such as sealing the tubing before replacing one of the dialysate bags.

In some embodiments, the at least one flow breaker allows, for example, to control the flow of fresh dialysate into the patient's catheter and/or from the patient's catheter into the draining bag.

According to some embodiments, a portable peritoneal (PP) dialysis system comprises a portable peritoneal (PP) dialysis machine including for example a durable unit, and a PP dialysis disposable, for example a disposable unit. Optionally the PP dialysis system comprises a PP patient management system.

In some embodiments, the durable unit comprises a motor, optionally an electric motor and electrical wiring and/or control circuitry for implementing a controller. In some examples, the PP dialysis machine includes a rotor with at least one roller (also: wheel). The rotor is operably coupled with a drive shaft of the electric motor. The motor, the drive shaft and at least some of the electrical wiring are part of the pump.

In some embodiments, the disposable unit comprises a tube with at least one connector. In some embodiments, the disposable unit is shaped and sized as a single unit keeping at least most of the disposable elements, for example, a tube and at least one connector encased in a separate housing from the durable unit. In some embodiments, the separate housing allows, for example, easy assembly ("pick-and-place") between the disposable unit and the durable unit, while protecting the disposable elements of the system. Additionally, the separate housing allows selling the disposable unit as a ready to use product without the need of further assembly of disposable elements by the user.

Figure 5H:
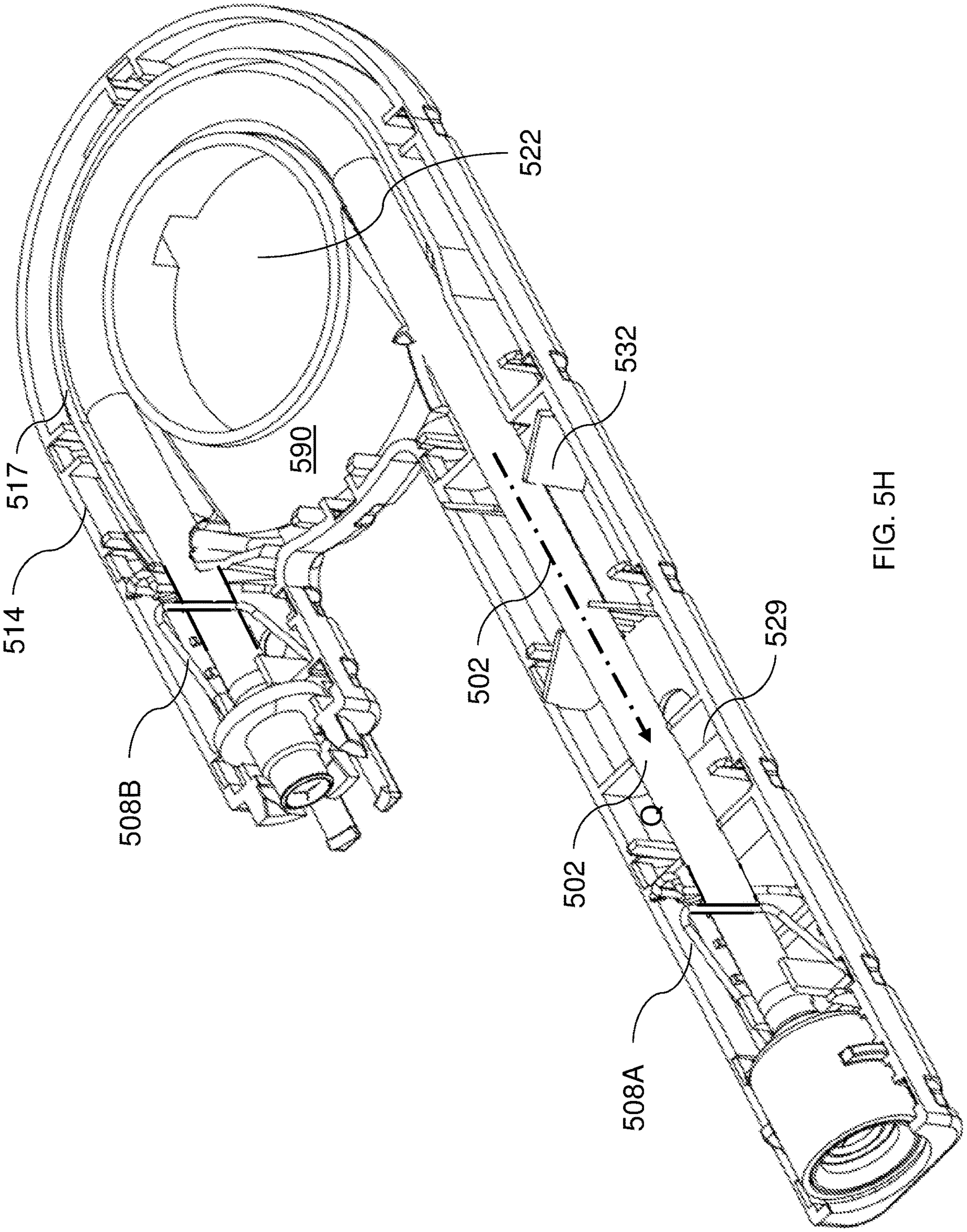
FIG. 5H is a schematic illustration of an upper part of the disposable cartridge, according to some embodiments.
Figure 5I:
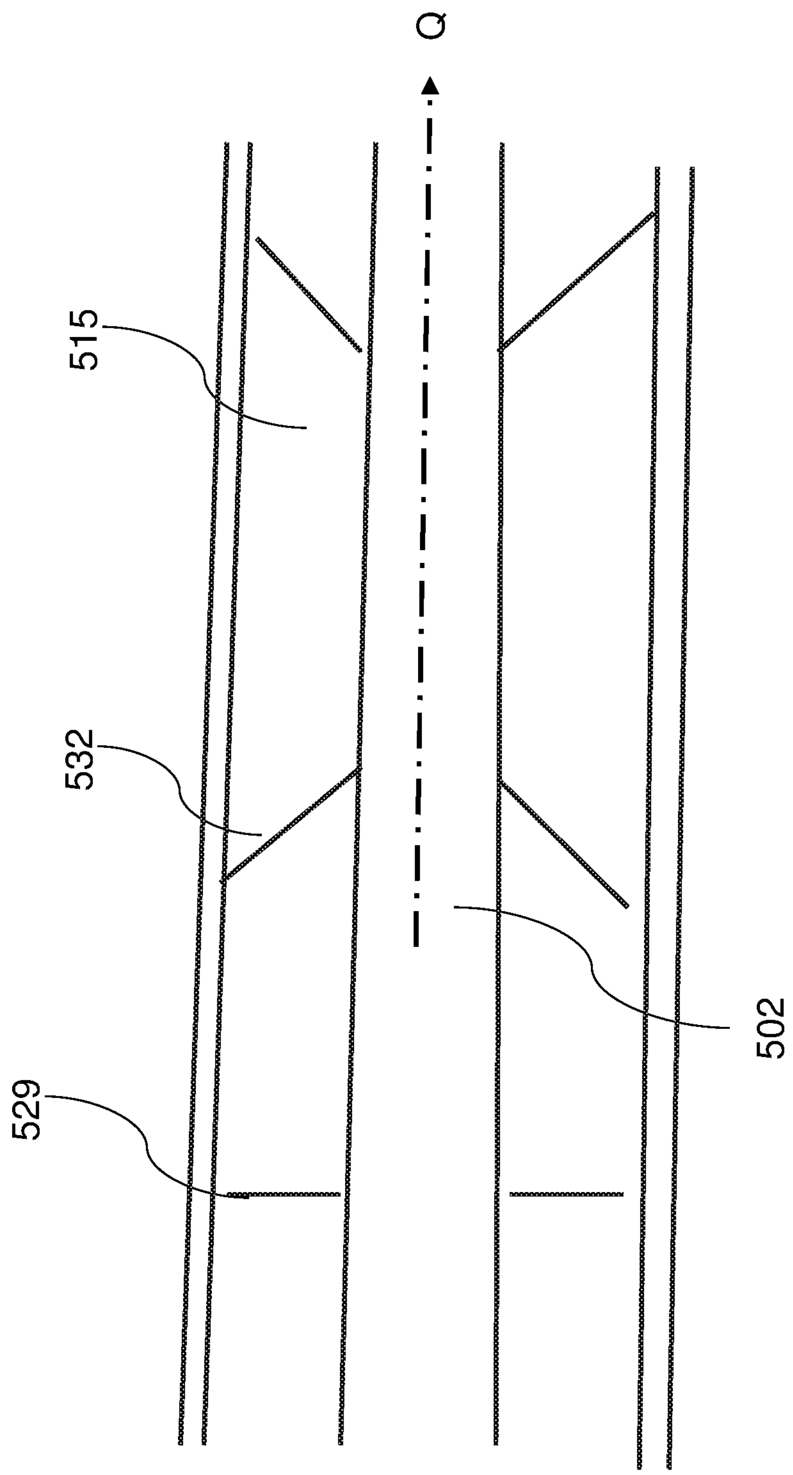
FIG. 5I is a schematic illustration of a section of the disposable cartridge, according to some embodiments.

Additional reference is made to FIGS. 5H and 5I. Figure H depicts a disposable unit 500 with one of its covers removed to show tubing 502 as it is held in place by flanges or fins 529. FIG. 5I is a diagram of a section of a tube guide 517 of with tubing 502, according to some embodiments. In some examples, tubing 502 may terminate in catheter connector 504 and/or in a Y-connector 506 suitable for fluid coupling with a Y-set tubing.

In some embodiments, the tube guide 517 includes tube holding or retention elements such as flanges or fins 529 to securely (e.g., frictionally) hold the tubing in place in tube guide 517 to prevent sliding and/or axial rotation of the tube while the pump is in motion. As a result, pressure sensing remains consistent as it is hardly, or not at all influenced by axial tube movement which might otherwise occur without the fins. Tubing may be pressed in between straight fins 529 and diagonal fins 532 to secure it in place. This assembly may be performed in the place of manufacture or by the user. Straight fins 529 are about orthogonal relative to tubing's 502 longitudinal axis Q, and diagonal fins 532 are angled relative to the longitudinal axis Q tubing 502.

Springs 508A and 508B are schematically shown in FIG. 5H to be in the closed configuration, applying pressure onto tubing 502 such to block the flow of fluid.

Figure 6B:
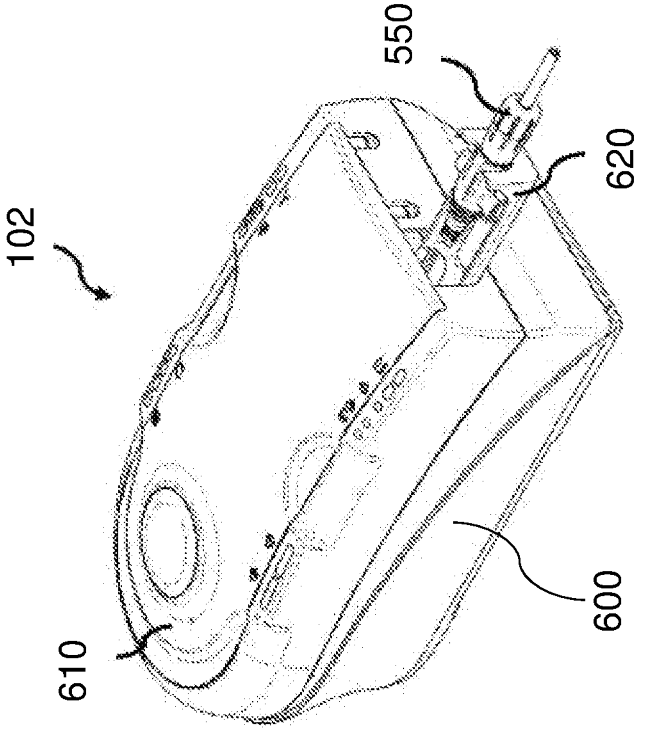
FIG. 6B is a schematic illustration of a dialysis device with its lid closed, according to some embodiments.
Figure 6A:
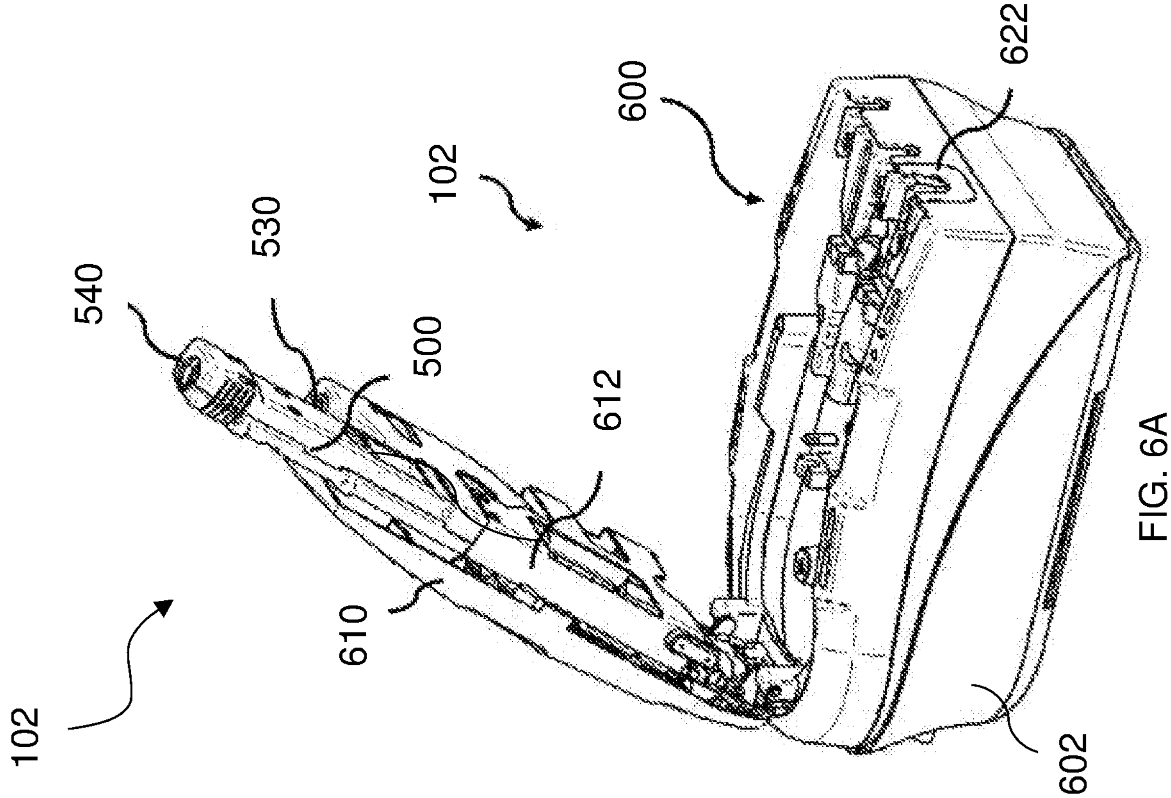
FIG. 6A is a schematic illustration of a dialysis device with its lid opened, according to some embodiments.

FIG. 6A illustrates a PP dialysis device 102 with the durable unit 600 in an open configuration and the disposable unit 500 partly inserted therein. FIG. 6B illustrates the PP dialysis device 102 with the durable unit in a closed configuration and an external catheter connector attached to an extended insertion tray 620.

In some embodiments, the disposable unit 500 is placed inside a PP dialysis machine, for example, durable unit 600. In some embodiments, durable unit 600 comprises at least one sensor positioned such that when the disposable unit 500 is positioned inside the durable unit 600, sensor (not shown) is proximal, and optionally aligned with a window 528 in the base part 512 through which tubing 502 can be viewed. In some embodiments, the sensor measures the absorbance of light optionally in specific wave lengths. In some embodiments, the sensor is a spectrophotometer.

In some embodiments, the at least one sensor measures absorption and/or scattering of light passing through the tubing in a wavelength range of 500-650 nm, for example in a range of 500-600 nm, in a range of 550-620 nm, in a range 530-630 nm or any intermediate, smaller or larger wavelength range. Additionally, or alternatively, sensor or at least one additional sensor measures absorption and/or scattering of light passing through the tubing in a wavelength range of 150-350 nm, for example 150-250 nm, 200-300 nm, 250-350 nm or any intermediate smaller or larger range of wavelengths.

According to some embodiments, at least one sensor or a testing element is connected to the tubing, for example to measure chemical and/or biological properties of the fluid the flows in the pump tubing.

Figure 6C:
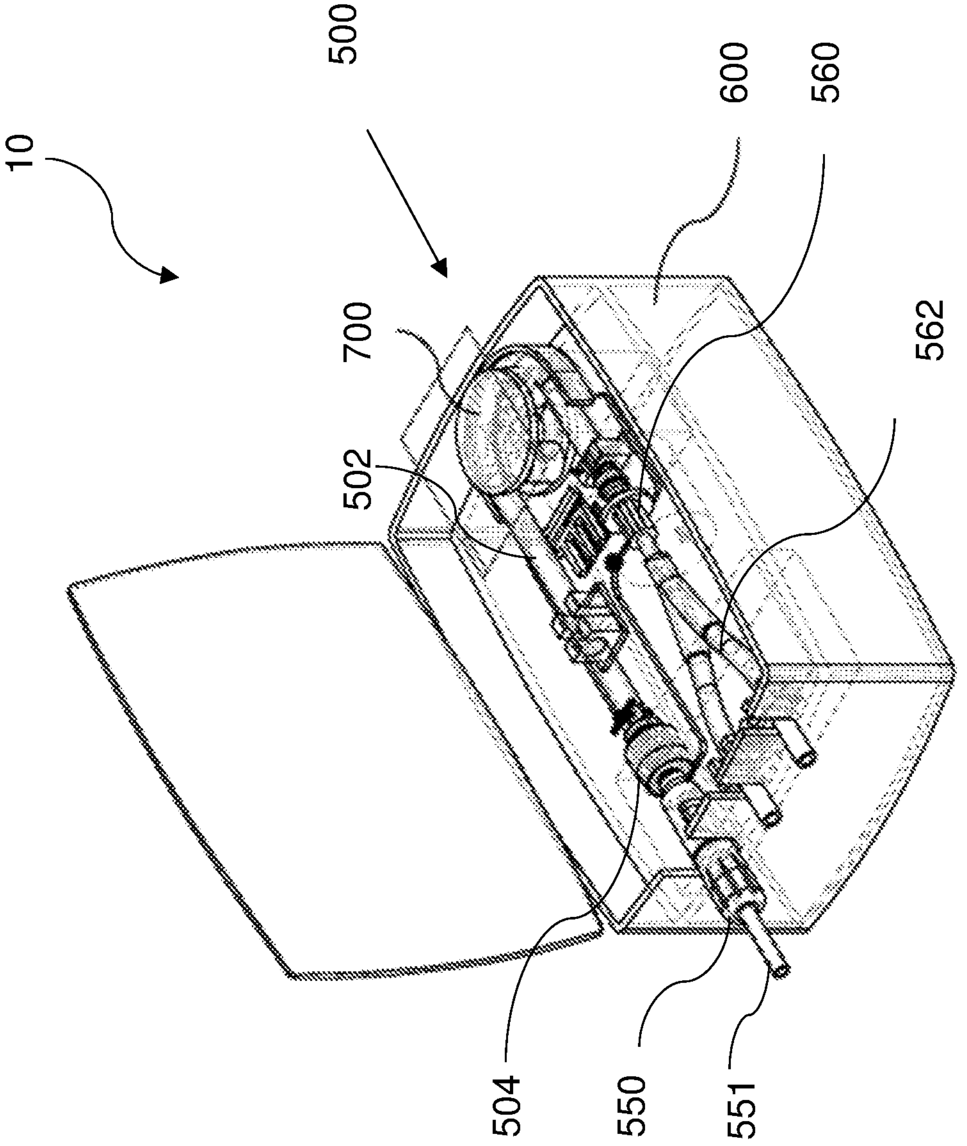
FIG. 6C is a schematic illustration of a dialysis device, according to some other embodiments.

Example Configurations of Disposable Unit of a Portable Peritoneal Dialysis Device FIG. 6C is an elevated isometric view of the PP dialysis system with the top cover casing laid open. According to some embodiments, a disposable unit of a PP dialysis system, for example disposable unit 500 comprises a tube 502 and at least one connector 506, for example for coupling with Y-set tubing 506, and catheter connector 504 located at the two respective ends of the tube 502. Optionally, tubing 502 is pre-filled with sterilizing fluid. Flow breakers 508A and 508B seal tubing 502 on the catheter end and the dialysate end, respectively. In some embodiments, connection of an external connector 550 to the catheter connector 504 automatically forces flow breaker 508 into the open state. In other embodiments, the flow breaker 508 can be manually, semi automatically or automatically manipulated into the open state or position. Once open, the sterilizing fluid flows into the external catheter connector 550, sterilizing the connector 550 and the catheter tubing 551.

In some embodiments, connection of Y-set tubing 506 from the dialysate bags to the dialysate tubing of Y-set tubing 506 automatically forces flow breaker 508 into the open state. In other embodiments, the flow breaker can be manually, semi automatically or automatically manipulated into the open state or position. Once open, the sterilizing fluid flows from the tubing 502 via the dialysate tubing of Y-set tubing 506 into Y-set tubing 506 and tubing 562, sterilizing the connector and tubing.

In some embodiments, the Y-connector can be positioned in either orientation. In some embodiments, one or more markers indicate which is drain and which is fresh dialysate fluid.

In some examples, where the Y-connector splits into two tubes there are two latches that can squeeze/unsqueeze the corresponding tube, depending on the stage of the cycle. These latches are referred to herein as flow breakers. In some embodiments a valve breaker is provided to prevent unwanted crossflow during transportation from the drained dialysate tube portion to the fresh dialysate tube portion.

According to some embodiments, the cover part 514 of the housing is mechanically connected to the base part 512 of the housing via connecting members, for example at least two threaded fasteners, screws, press-fit connectors, latch connectors and/or the like. In some embodiments, the threaded fasteners comprise screws and/or bolts. In some embodiments, the two connecting members comprise pins. In some embodiments, each of the at least two connecting members penetrates through opening in the cover part, for example opening 524 and into an opening in the base part, for example base part opening 526. Optionally, the base part opening comprises an internal threading complementary to an external threading on the connecting member.

According to some embodiments, for example as shown in FIGS. 5E-5G, the disposable unit 500 has at least two openings in the housing, openings 530 and 540. In some embodiments, one opening 540 is shaped and sized for connection of an external catheter connector 550 to catheter connector 504 and optionally a second opening 530 for connecting Y-set tubing 506. In some embodiments, at least one marking on the external surface of the housing indicates, for example an assembly direction and/or orientation of the disposable unit into a durable unit.

As schematically depicted in the embodiment, disposable unit 500 is inserted into durable unit 600 in the movable lid piece. After insertion of the disposable unit and the Y-set tubing, the lid is closed, sandwiching the pump tubing between the wheels and the casing. Even prior to start of pumping, the rim surface of at least one of the wheels compresses the tubing to at least partially, and in some cases completely, restrict flow between two sides of the compressed area. This compression of the tube serves to divide the sterilizing fluid into two compartments: one compartment from the flow breaker adjacent the catheter connector to the rotor wheel and the second compartment from the other side of the wheel to the flow breaker adjacent the Y-set connector. When so compressed, the fluid can be released through either of the flow breakers without emptying sterilizing fluid from the other compartment.

In some embodiments, the disposable elements are placed within shaped grooves or indentations made in the internal surface of the disposable unit housing, for example a two-part housing. In some embodiments, the grooves or indentations are made in the internal surface of at least one part of the two-part housing, for example in a base part 512. In some embodiments, the two-part housing comprises a complimentary cover part 514, shaped and sized to match the base part 512. In some embodiments, the cover part 514 comprises grooves or indentations that match at least part of the three dimensional shape or external contour of the disposable elements within the base part 512.

According to some embodiments, for example as shown in FIGS. 5E and 5E the base part 512 and the cover part 514 are assembled into housing 515 of the disposable unit 500. In some embodiments, the axial length 516 of the housing 515 is at least 10 cm, for example 12 cm, 15 cm, 19 cm, 20 cm, 25 cm or any intermediate, smaller or larger value. In some embodiments, the width 518 of the housing 515 is at least 1 cm, for example 1.5 cm, 2 cm, 2.5 cm or any intermediate, smaller or larger value.

According to some embodiments, the housing is shaped to allow easy assembly into the durable unit and/or easy assembly of external tubes to at least one connector of the disposable unit. In some embodiments, the cover part 514 can be integrally formed with the lid of the durable unit.

In some embodiments, cover part 514 comprises an opening above the rotor, for example upper opening 522. In some embodiments, the upper opening 522 allows, for example to visualize the rotation direction of the rotor. Cover part 514 around upper opening 522 may be adapted to hold the curved portion of the pump tubing 502.

According to some embodiments, for example as shown in FIGS. 5E and 5E, the base part 512 comprises a base opening 520 which may be larger than cover opening 522 and is shaped and sized to allow the rim surfaces 720 of the at least one wheel 710 of the rotor 700 to compress the compressible tube 502.

When assembled, the disposable unit interfaces with at least one sensor disposed on the facing surface of the durable unit. The at least one sensor includes any of the examples of sensors have been detailed elsewhere herein. Furthermore, in some embodiment there are sensors on the wheels to monitor if there is disconnection or imbalance of the tube.

In some embodiments, the system comprises a light source. The at least one sensor is configured to measure light absorption and/or light scattering of light emitted by the light source to detect and, optionally, count bubbles in the dialysate fluid and/or to determine fluid quantity and/or flow velocity, e.g., based on the detection of bubbles.

In some embodiments, the device comprises a tilting mechanism, for example to allow release of air bubbles from the fluid flow path. In some embodiments, when priming the device, precautions are taken to ensure air removal. Furthermore, monitoring for bubbles (and their removal) is ongoing throughout the procedure.

For example, if bubble diameter is larger than a threshold, then the bubble is removed through reversing the flow to drain.

The fluid flow can be measured using techniques known in the art. In this regard, bubbles that have been detected but determined to be below the threshold are allowed to remain in the tube but must be accounted for, by subtracting the volume of the air bubbles.

Reference is now made to FIGS. 6A-6C, depicting the assembly of a disposable unit 500 into a durable unit 600, according to some embodiments.

According to some embodiments, the durable unit, for example durable unit 600, comprises a base 602 and a door or cover 610.

Durable unit 600 may be configured such that cartridge 500 is receivable in alignment with pump rotor 700 such that, when assembled, tube included in cartridge 500 is operably engaged with pump rotor 700. In some examples, durable unit 600 may include an aligning slot 612 to configured to receive cartridge 500 in alignment with pump rotor 700. In some examples, door 610 may include aligning slot 612.

In some embodiments, at least part of the door 610 is transparent, for example to allow visualization of a disposable unit placed inside the durable unit or a rotor of the durable unit. In some embodiments, a disposable unit, for example disposable unit 500 is shaped and sized to inserted into the aligning slot 612, for example as shown in FIG. 6A. In some embodiments, the disposable unit 500 is inserted into the aligning slot in a direction and/or orientation indicated by at least one mark on the housing of the disposable unit 500.

According to some embodiments, after the insertion of the disposable unit 500 into the aligning slot 612, the door 610 is closed.

In some embodiments, an external Y-set connector 560 is connected to Y-set tubing 506 through opening 530 prior to the closure of the door 610 or prior to the insertion of the disposable unit 500 into the aligning slot 612. In some embodiments, Y-set tubing 506 is connected to external Y-set connector 560, e.g., through opening 530.

According to some embodiments, for example as shown in FIG. 6B, when the door 610 is closed, a drawer of the durable unit 600, for example drawer 620 is extended out from the durable unit housing. Optionally, the drawer 620 is extended automatically when the door 610 is closed. In some embodiments, the drawer 620 comprises an upper opening and a side opening 622, optionally a U-shaped side opening, for placing a catheter end 550.

According to some embodiments, when the drawer 620 is closed, the catheter end 550 is pushed into the catheter connector 504. In some embodiments, when the catheter is connected through the catheter connector 504, a disinfection process is initiated. The disinfection process is discussed elsewhere herein.

According to some embodiments, dialysis device 102 activates a motor, for example an electric motor to move disinfecting material through the tubing of the disposable unit and dialysate into and out from the peritoneum of a patient through a catheter connected to the system. In some embodiments, the dialysis device comprises at least one battery, optionally a rechargeable battery. In some embodiments, dialysis device 102 comprises a charging plug (not shown), for connecting an external power source to the rechargeable battery, for example to allow charging of the battery. Alternatively, the connection of the external power source to the dialysis device, allows to activate the device using the external power source instead or in addition to the battery.

According to some embodiments, the housing of dialysis device 102, comprises at least one adapter for example for connecting a belt or a harness to the dialysis device. In some embodiments, the belt or the harness is used to secure the dialysis device to a body part of a patient, for example to the hand, leg, shoulder, thigh and/or hips of the patient.

According to some embodiments, dialysis device 102 may be portable and configured to be secured to a body part of the patient by a belt, a harness or any adaptor. In some embodiments, the dialysis device comprises a durable unit which comprises a motor, for example an electric motor and a battery, optionally a rechargeable battery electrically connected to the rotor. In some embodiments, the durable unit comprises a control circuitry electrically connected to the motor and to the battery.

Figure 7A:
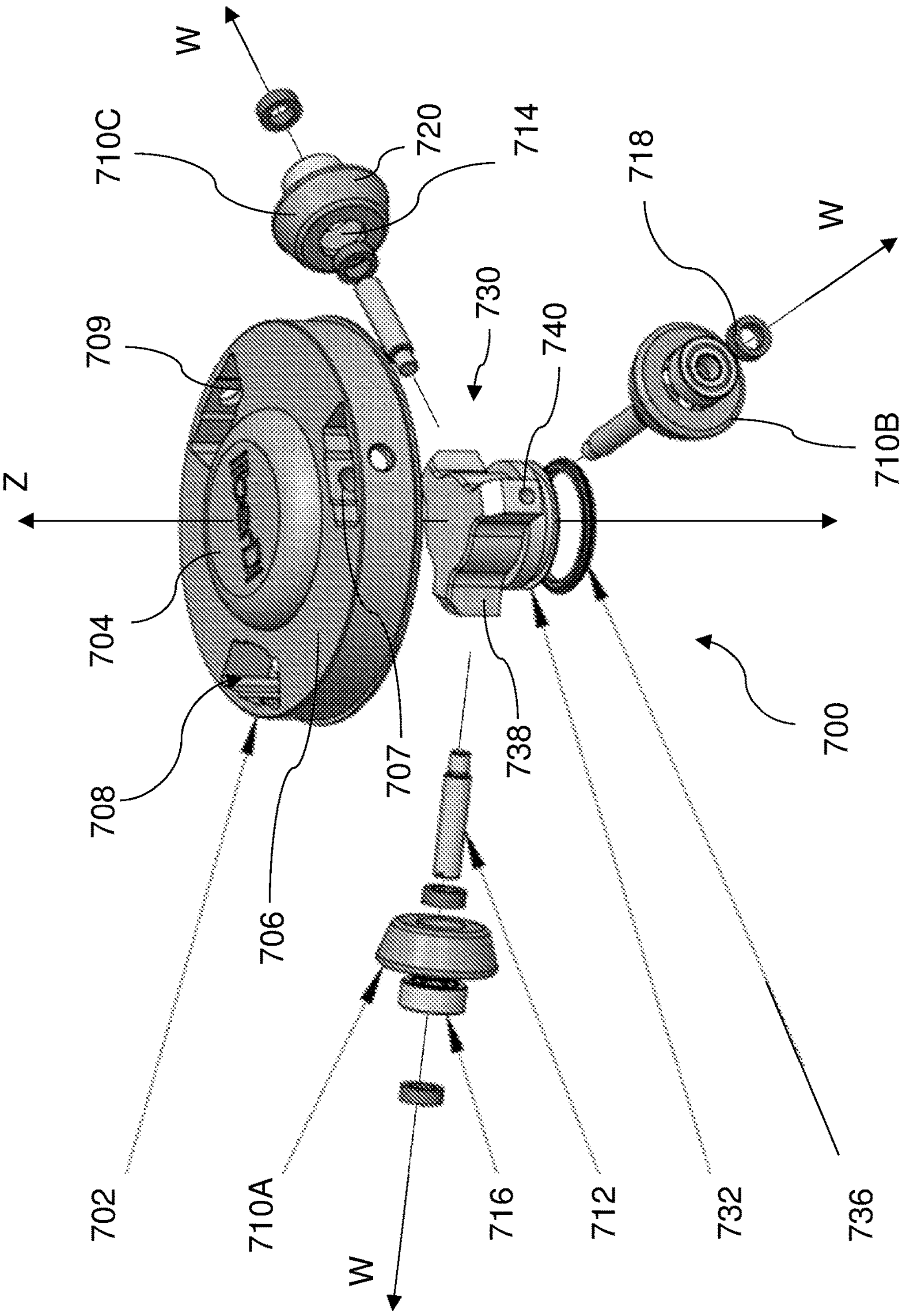
FIG. 7A is a schematic exploded view of a pump rotor, according to some embodiments.
Figure 7D:
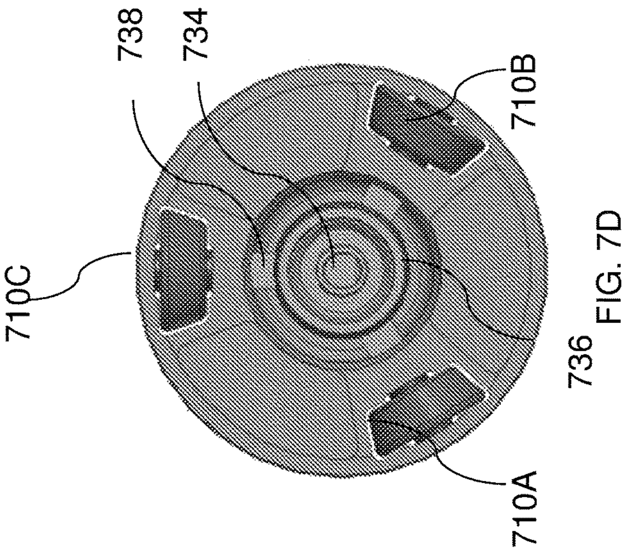
FIGS. 7B-7E are different schematic views of the pump rotor, according to some embodiments.
Figure 7C:
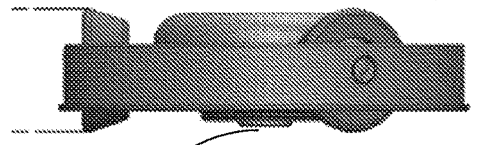
Figure 7B:
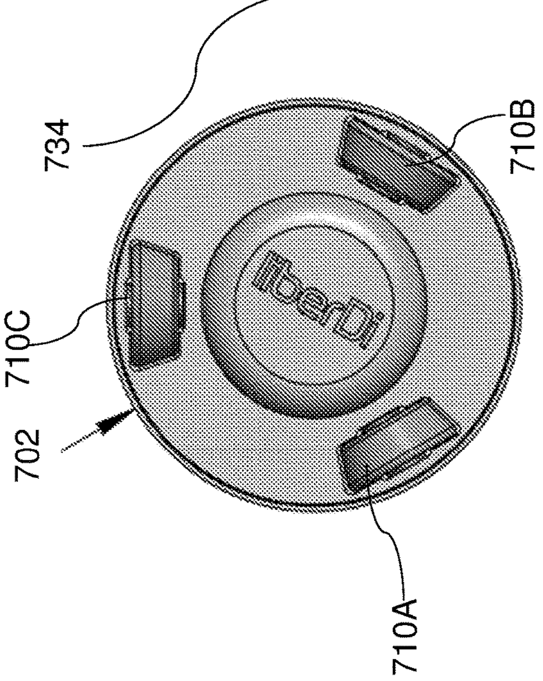
Figure 7E:
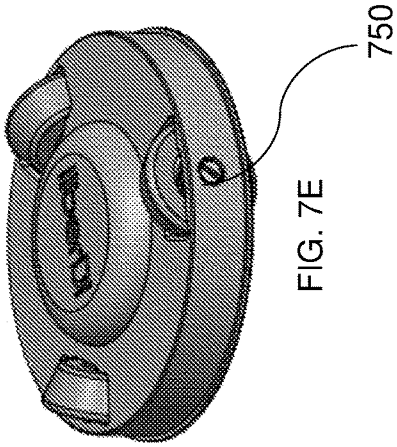

FIG. 7A is an exploded view of a pump rotor 700. FIG. 7B is a top-down view of rotor 700. FIG. 7C is a side view of pump rotor 700. FIG. 7D is a bottom-up view of rotor 700. FIG. 7E is a two-dimensional 3D representation of pump rotor 700.

In some embodiments, durable unit 600 comprises a complete pump assembly and the disposable unit or cartridge 500 is operably engageable with complete pump assembly in a pick-and-place step.

The pump assembly includes pump rotor 700 that is operably couplable with a pump drive (not shown), including a shaft for rotating pump rotor 700.

The pump rotor 700 has a rotor rotation axis Z that is normal to a rotation plane of the pump rotor. The rotor 700 has at least one wheel 710 that is rotatably coupled (e.g., by bearings) with the pump rotor 700. Each wheel of the at least one wheel 710 has a wheel rotation axis W that is perpendicular to the rotor rotation axis Z. When activated, rotation of the pump rotor about the rotation axis Z causes rotation of the at least one wheel 710 about the wheel rotation axis W such that the at least one wheel traverses a circular path around the rotation axis Z and compresses a corresponding portion of tubing 502, which is a compressible tube in a direction which is in direction of the pump rotor rotation axis Z. Rotation of pump rotor about the rotation axis Z causes wheel rotation axis W to circulate about the rotor rotation axis Z in the rotor rotation plane. The pump motor is bi-directional and, accordingly, the rotation direction of the rotor is reversible.

In some examples, when the rotor direction is from the catheter connector side to the dialysate connector side, i.e., a clockwise direction according to the depicted, embodiment, the pump forces fluid from the catheter to the dialysate bags. In this direction, the fluid is drained from the peritoneal cavity to the dialysate drainage bag.

For example, when the rotor direction is from the dialysate connector side to the catheter connector side, i.e., an anti-clockwise direction according to the depicted, embodiment, the pump forces fluid from the dialysate bags to the catheter and into the peritoneal cavity. In this direction, the new dialysate fluid is pumped from dialysate bag into the peritoneal cavity.

Pump rotor 700 includes a main housing 702 that houses at least one wheel 710 (e.g., wheels 710A-C). The at least one wheel 710 has a rim surface configured to offset for possible differences in angular velocity when circulating about the rotor rotation axis Z. In some embodiments, the at least one wheel 710 has a rim surface 720 tapering towards the rotor rotation axis Z. In embodiments, the rim surface is that of a frustum. In the depicted embodiment, the housing houses three wheels 710.

In some examples, the top portion of the housing 702 may include, for example, a dome section 704 e.g., located in the center of the housing, and a plateau section 706 surrounding the central dome section. In some examples, the top portion may only comprise plateau section 706. In some embodiments, the opening 520 is shaped and sized to allow the dome section 704 of the housing 702 to pass therethrough.

The plateau section 706 includes at least one opening 708 configured to rotatably receive at least one wheel 710, respectively. In the depicted example pump rotor, there are three wheels 710A, 710B and 710C which are about equally spaced around the periphery of the plateau section 706.

The bottom portion of the housing has a central opening below the dome section and three additional openings below the plateau section. The additional openings are positioned in correspondence with the openings in the top portion.

When assembled, the at least one rotor wheel 710 applies force onto the tube portion that is located below the rotor wheels from the bottom upwards or, for example, in a direction which is about parallel to the rotor axis Z, for squeezing and elastically deforming the tube portion and thereby move fluid in the tube along the rotor's rotation direction. The rotor may be part of the durable unit.

The cover part above the tube that interfaces with (e.g., rotatably receives) the pump wheels may be angled in a manner that corresponds to the angle of the wheels. The angled 'roof' increases or maximizes the contact region between the wheels and the wheel-interfacing roof portion, e.g., to prevent the pump from 'skipping' at the end of each revolution.

Sensors on the wheels detect if there is disconnection or imbalance of the tube. The sensors may for example be included in the pump, the disposable unit and/or the roof. In some embodiments, the rotor is supported (and buoyed) by mechanical storage elements (e.g., springs).

In some embodiments, each wheel is supported by a mechanical storage element. The rotor and wheels are designed to provide sufficient force on the tube for the pump action but at the same time taking care to prevent tearing or other damage to the tubing. In some examples, excess pressure applied onto the tube by the rotors may be detected, and a corresponding output may be generated by the system.

In some example configurations, a sprocket or hub 730 is seated in the central opening of the bottom portion of the housing 702, as shown for instance in FIG. 7D. The central hub includes a collar 732 which couples to the pump motor. The shaft of the motor couples extends into an aperture 734 inside collar 732. Aperture 734 is disposed centrally, on the underside of the hub 730. An O-ring 736 surrounds a terminal end of the collar to form a watertight connection with the motor.

In the embodiment depicted in the Figures, hub 730 has (e.g., three) radially extending protrusions 738, one for each of the wheels 710. Each of the protrusions has a pin hole 740 for receiving a rod 712. The rod 712 couples the wheel to the housing 702. Rod 712 extends from the hub, through openings 707 and terminating in (e.g., screw) holes 709. The rod 712 may have internal threading.

Each of the at least one wheels 710 has a ball bearing 716 disposed within the central opening 714. Two spacers 718 abut the wheel on each side. The spacers position the wheel centrally within the wheel opening 708 in the housing. During assembly of the rotor, the rod 712 is inserted via the screw hole 709 and the first spacer 718, the wheel 710 with the ball bearing 716 and the second spacer 718 are loaded onto the rod 712. Hub 730 is installed in the opening of the bottom portion of the housing, below the dome. Rod 712 is then pushed through opening 707 and into pin hole 740. The assembly is secured by a securing element (e.g., a screw or bolt) 750 which is inserted through screw hole 709 and screwed into rod 712. For example, if securing element 750 is implemented as a screw, rod 712 has internal threading that is complementary to the external threading of the screw.

Pump assembly or pump includes a shaft extending from the pump motor and operationally coupling to the pump rotor. The shaft is configured to operably receive the pump rotor thereon. For example, the shaft may be configured to receive the rotor in a pick-and-place assembly step in direction of the rotor rotation axis Z.

The circular section of the upper casing or cover part 514 of the disposable unit 500 completes the pump assembly. The pump tubing 502 is a compressible tube having a channel or internal volume for fluid flow. When operably assembled with the pump rotor, the compressible tube is sandwiched between the rim surface 720 of the at least one wheel 710 and the circular section of the upper casing of the disposable unit 500.

Figure 8A:
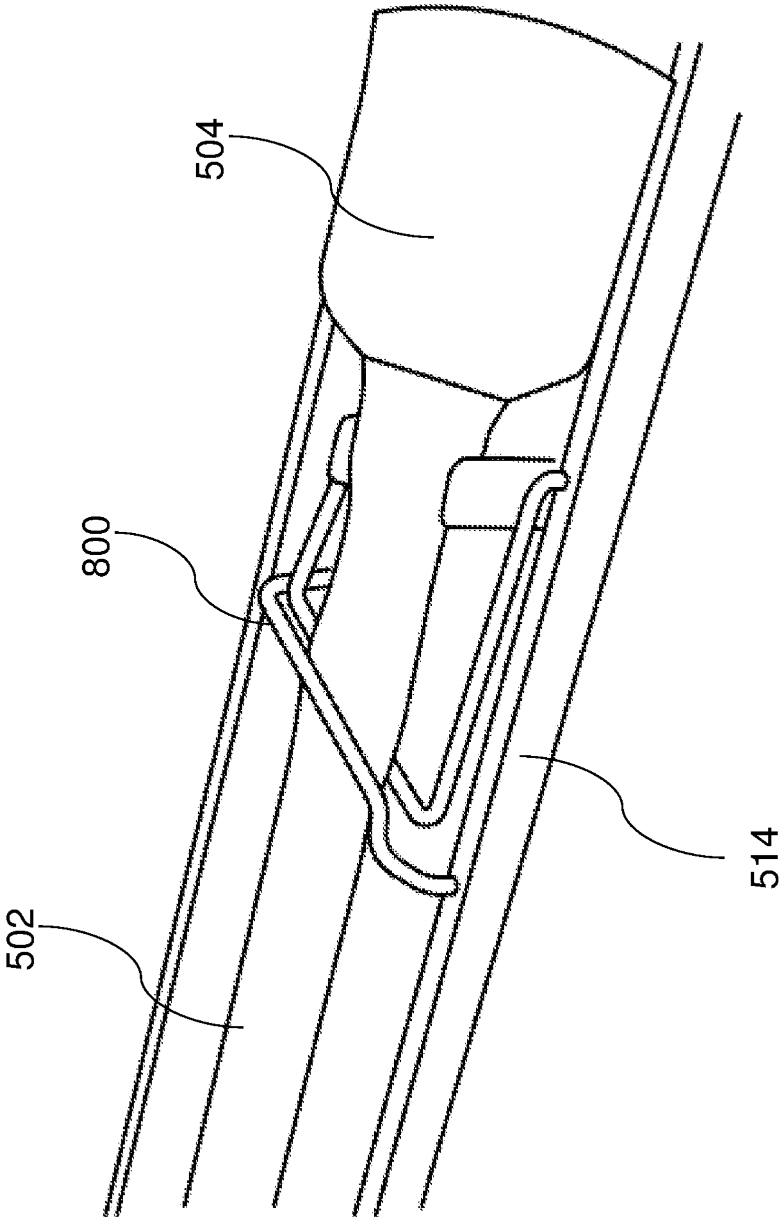
FIG. 8A is a schematic illustration of a flow breaker in a closed configuration, operably engaging with the tubing, according to some embodiments.
Figure 8B:
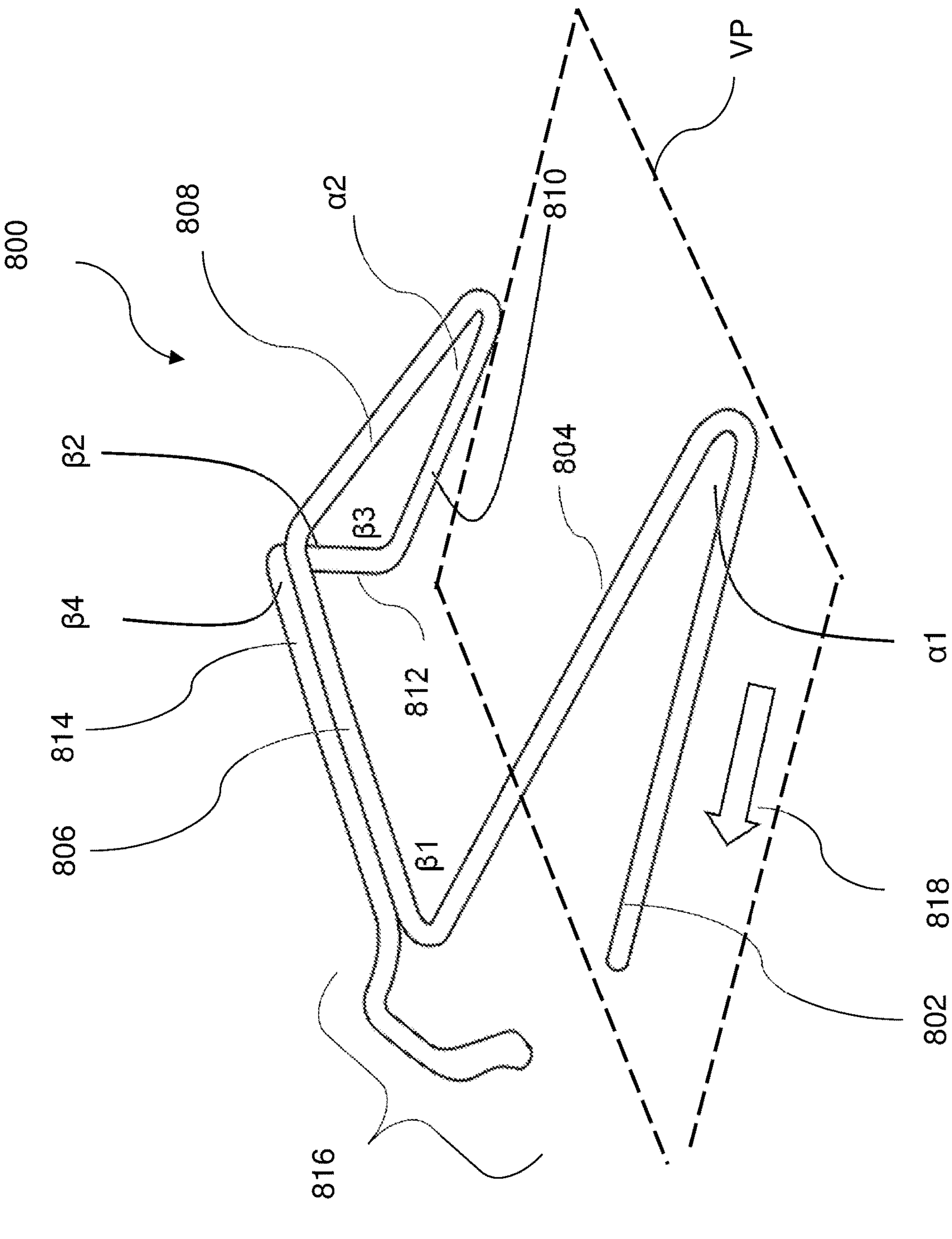
FIG. 8B is a schematic illustration of the flow breaker of FIG. 8A in the closed configuration, according to some embodiments.
Figure 8C:
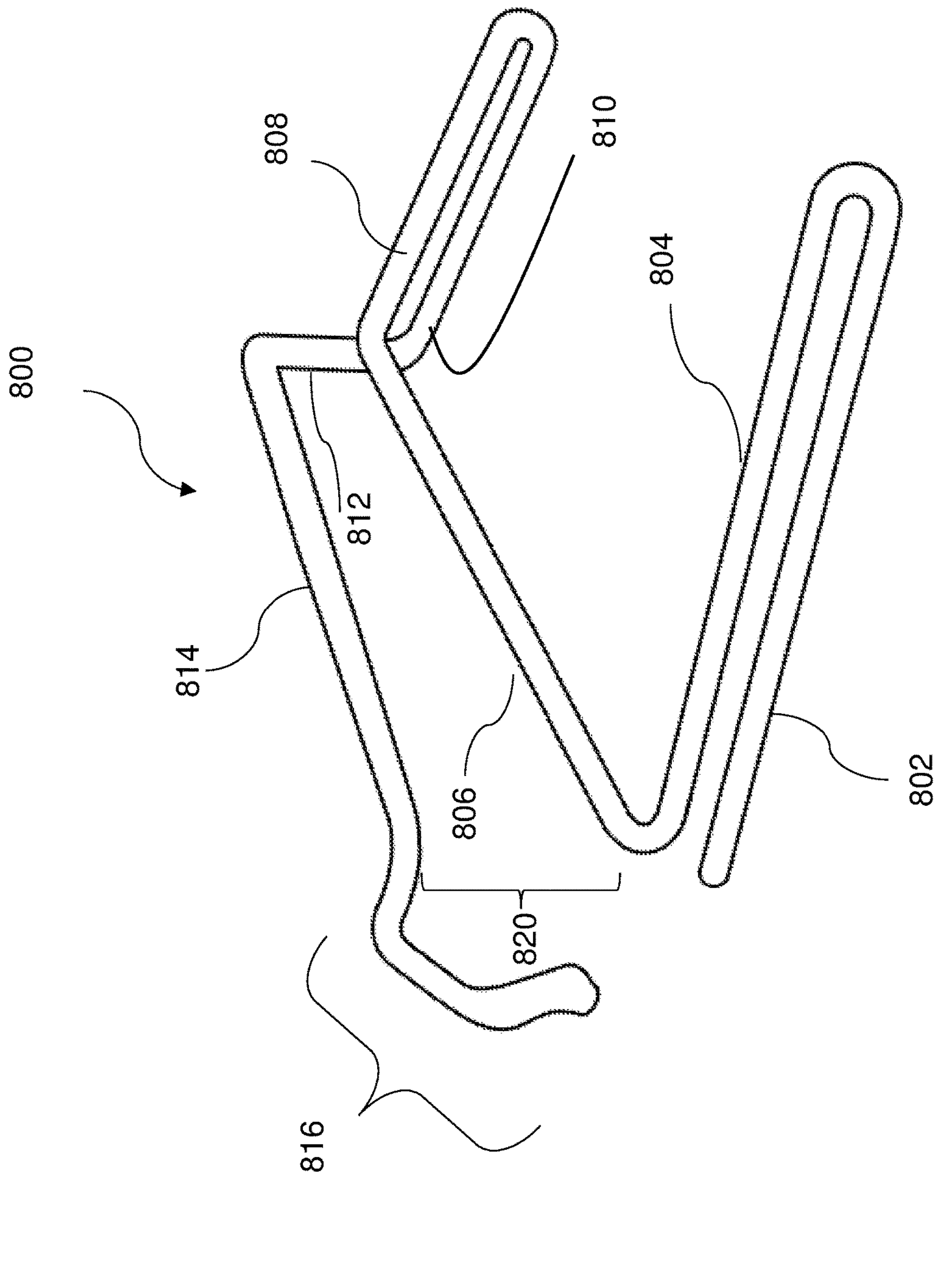
FIG. 8C is a schematic illustration of the flow breaker in the opened position, according to some embodiments.

As briefly mentioned herein above, FIG. 8A and FIG. 8B depicts a flow breaker comprising or implemented by a spring member 800 in a closed configuration. FIG. 8C depicts spring member 800 in an open configuration. Spring 800 serves to selectively restrict or allow flow of fluid within tubing 502.

Spring 800 may be formed from a single metal wire that has elastic properties, returning to an initial form, even after being deformed. Wire 800 has several sections. Each section may be angled away from the subsequent, abutting section.

A first section 802 of the wire is substantially parallel relative to a virtual reference plane VP, which is about parallel to the floor of the system's base part. The wire may have a second sequential section 804 that is angled apart from the first section, away from the reference plane. The first and second sections form an angle $\alpha 1$. In some examples, angle $\alpha 1$ is about 45° (45 degree) angle. In other embodiments, the angle $\alpha 1$ can be any angle between about 35 and about 65 degrees.

The wire may have a third sequential section 806 that is angled apart from the second section. The second and third sections form an angle $\beta$. In some examples, angle $\beta$ is an about 90° (90 degree) angle or a right-angle. Third section 806 is elevated from, and perpendicular to, first section 802 and about parallel to the reference plane.

The wire has a fourth sequential section 808 that is angled apart from the third section 806. The third and fourth sections form an angle β2. In some examples, angle β2 is an about 90° (90 degree) angle or a right-angle. The fourth section may be about perpendicular to the third section and parallel to the second section 804. The fourth section 808 may extend from the third section 806 downward towards the reference plane, optionally about parallel to second section 804.

A fifth section 810 of the wire sequentially follows the fourth section 808 and is substantially parallel relative to the virtual reference plane. The fifth sequential section 810 is angled apart from the fourth section. The fourth and fifth sections form an angle α2. In some examples, angle α2 is about 45° (45 degree) angle. In other embodiments, the angle α2 can be any angle between about 35 and about 65 degrees. Fifth section 810 is parallel to first section 802. First section 802 and fifth section 810 may define the reference plane.

A sixth section 812 of the wire sequentially follows fifth section 810 and is substantially vertical, extending upwards away from the reference plane, forming about a 90° (90 degree) angle or a right-angle β3 with fifth section 810.

A seventh section 814 of the wire sequentially follows the sixth section 812 and is about parallel to the reference plane, forming a 90° (90 degree) angle or a right-angle with the sixth section. Sections seven and three run nearly parallel to each other and define a clamping area between the two sections where they abut and even touch each other in places.

An eighth section 816 sequentially follow the seventh section 814. The eighth section is the last, terminal section of the spring and has a complex form that is shaped to secure the spring in a corresponding groove or hole in the base part 512 of the disposable unit 500.

In use, either of sections two 804 or four 808 can be biased towards sections one 802 or five 810 to move the spring from the resting position (closed state) to a biased condition/position (open state) as depicted in FIG. 8B. In use, as depicted in FIG. 5D, sections 806 and 814 clamp onto the tube 502. In some examples, a biasing member can be a C-shaped element with a flat middle section and two perpendicular side sections. The biasing member runs in the direction of arrow 818 where one side section runs under the first section 802 and the other side section runs over the second section 804, forcing the second section closer to the first section and widening the clamping area between sections three 806 and seven 814 as depicted in FIG. 8B.

Optionally, the biasing member may be part of the base part 512 or cover part 514 or held between the two. The spring can be returned to the closed state by moving the biasing member in the reverse direction (i.e., in the direction opposite the direction of arrow 818).

Figure 8D:
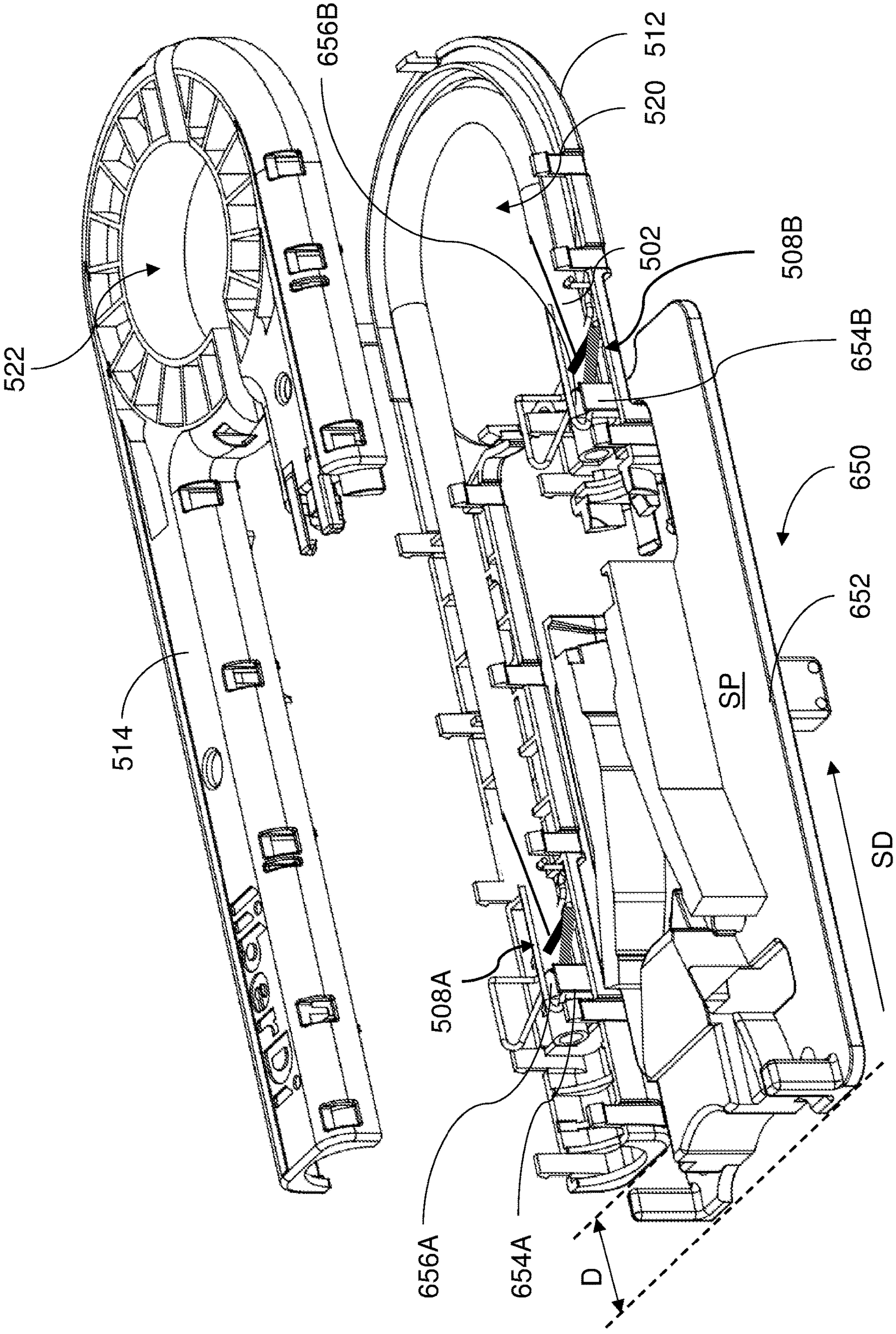
FIG. 8D is a schematic illustration of the disposable part and of an actuator in a retracted position such that the flow breaker is in the closed configuration, according to some embodiments.
Figure 8E:
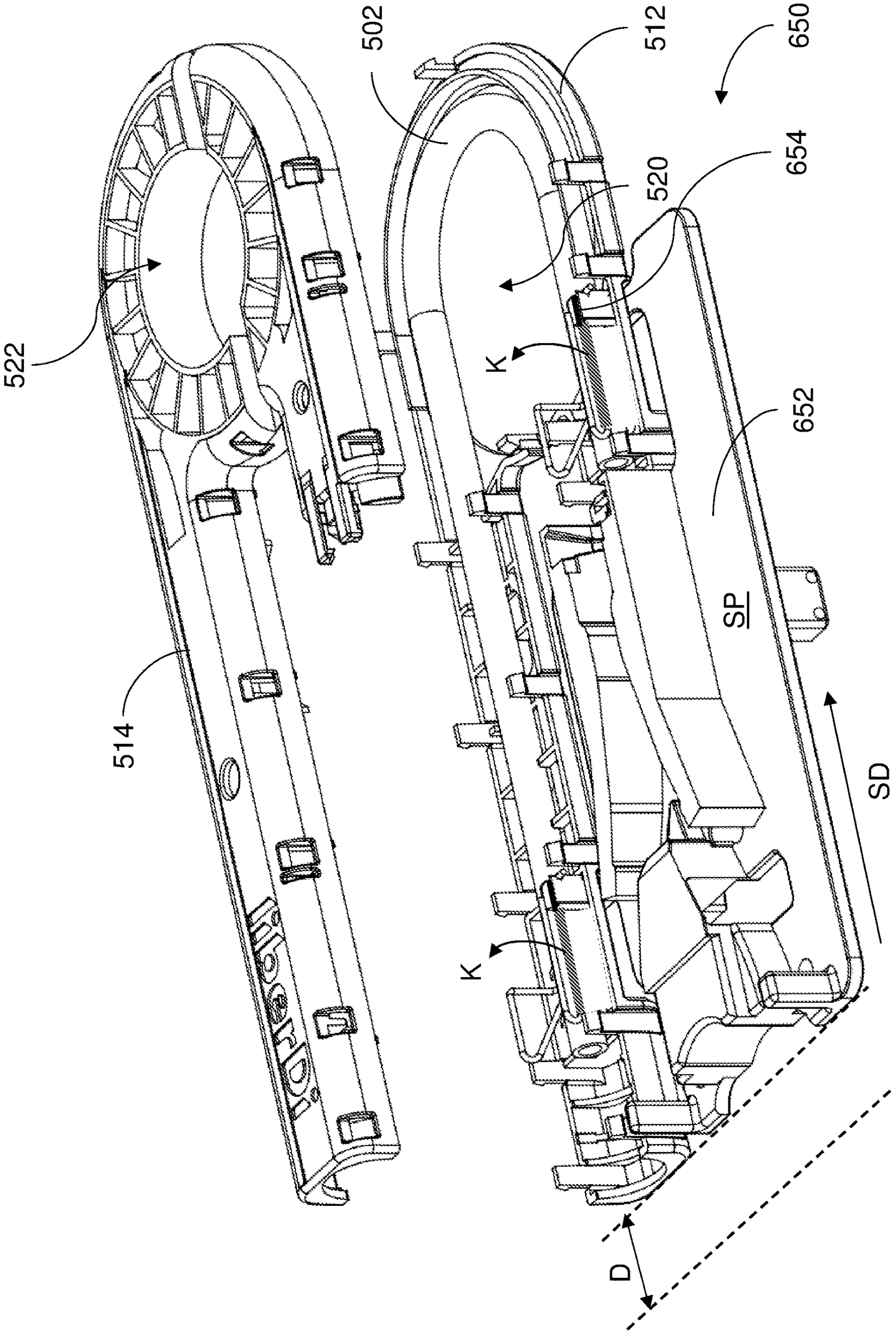
FIG. 8E is a schematic illustration of the disposable part and of the actuator in an advanced position causing the flow breaker to be in the open configuration, according to some embodiments.

Additional reference is made to FIGS. 8D and 8E. Dialysis system 100 includes an actuator that is controllably actuatable to engage with a flow breaker for selectively setting the flow breaker into the open configuration, allowing fluid to flow through the tubing, or the closed configuration to reduce or prevent flow of fluid through the tubing. Such actuator may for example be comprised in durable unit 600.

For example, an actuator may include a slider platform 650 comprising a biasing element 654 that is fixedly coupled with the slider platform 650. In some examples, slider platform 650 may be part of durable unit 600.

In some embodiments, an actuator (also: slider drive) (not shown) may be operatively coupled with slider platform 650 for controllably causing actuation of the slider platform. In either case, the slider platform is controllably slidable in a sliding direction S for actuation (i.e., controllably changing a state) of the flow breaker. The sliding direction SD may lie in a sliding plane, e.g., which is about parallel to a tubing plane delineated by a fluid flow path defined by tubing 502. To simplify the discussion that follows, slider plate 652 is considered to lie on or define the sliding plane SP. In the example configuration shown, biasing element 654 extends vertically from the plate 652 or sliding plane SP.

When slider plate 652 is in a retracted, first position (FIG. 8D), third sequential section 806 is set in an unbiased state and flow breaker 508 is set in the normally closed configuration, in which tubing 502 is sandwiched or pressed two spring wire section, e.g., between third wire section 806 and seventh wire section 814.

Biasing element 654 may have a groove 656 configured to slidably receive second sequential section 804 of wire 800. When slider plate 652 slides from the retracted position to an advanced, second position (FIG. 8E) by traversing a distance D in a sliding direction SD, biasing element 654 correspondingly advances from the first position to the second position, causing groove 656 to apply a force onto second wire section 804 and bend second wire section 804 towards first wire section 802, thereby causing third wire section 806 to move away from seventh wire section 814.

Moving away third wire section 806 from seventh wire section 814 (as schematically illustrated by arrows K) causes the creation or the increase of a gap 820 between third wire section 806 and seventh wire section 814 and, therefore, decompression of the pressure that was applied before by third wire section 806 and seventh wire section 814 onto tubing 502. The decompression and creation of gap 820 allows increased flow of fluid such as fresh dialysate, used dialysate, and/or of disinfection material, through tubing 502.

Figure 8F:
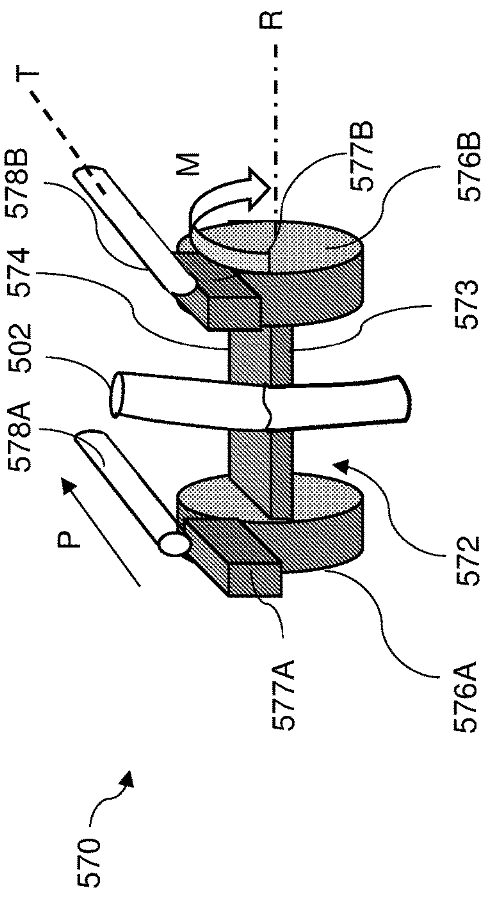
FIG. 8F is a schematic illustration of a flow breaker in a blocking configuration, according to some other embodiments.
Figure 8G:
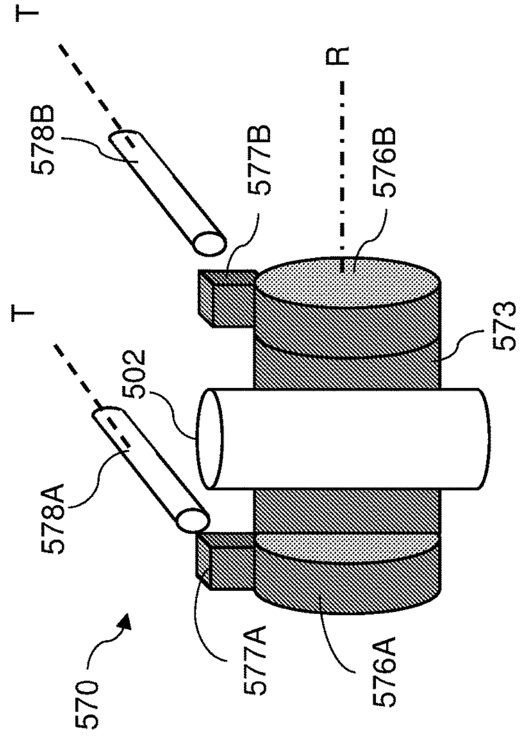
FIGS. 8G and 8H are a schematic illustrations of the flow breaker of FIG. 8I in an open or non-blocking configuration, according to some other embodiments.

Further reference is now made to FIG. 8E to FIG. 8G. In some embodiments, a flow breaker 570 may be implemented by employing a rotatable blocking element 572 which rotatable from a first (closed configuration), preventing or reducing flow of fluid through tubing 502, to a second (open) position, enabling substantially unobstructed flow of fluid through tubing 502.

Rotatable blocking element 572 may for example include a plate having a front edge 573 and a rear edge 574, opposite the front edge 573. Merely for the purposes of the discussion therein, front edge 573 may refer to the plate edge that is, with respect to the fluid flow path defined by tubing 502, closer to the catheter connector 504 than to Y-set connector 560 of the disposable unit 500.

In some embodiments, rotatable blocking elements 572 is biased to be in the closed configuration, for example, by a mechanical storage element (e.g., a torsion spring).

In some embodiments, rotatable blocking element 572 is biased to be in the open configuration, for example, by a mechanical storage element (e.g., a torsion spring).

In some embodiments, rotatable blocking element 572 is idle with respect to the open and closed configuration.

Figure 8H:
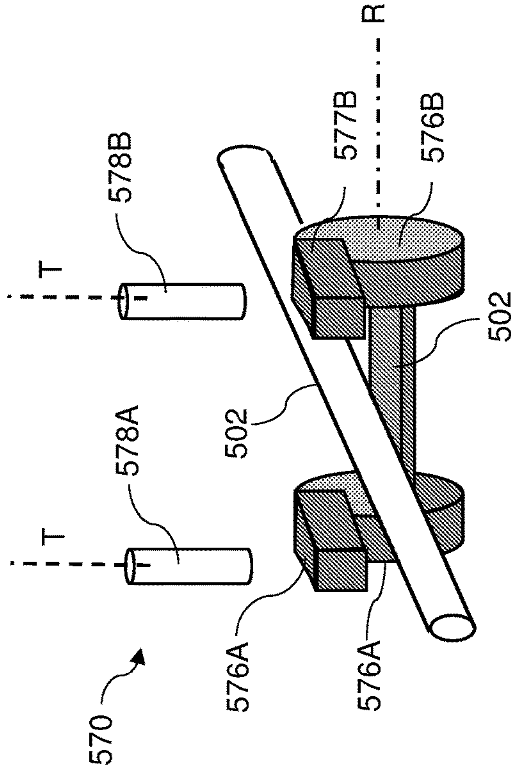

In the examples discussed herein with respect to the FIGS. 8F-8H, blocking element 572 is in "normally open" position, shown in FIG. 8F.

FIG. 8F shows rotatable blocking element 572 in the closed configuration, such that front edge 573 presses against tubing 502 obstructing the flow of fluid. Blocking element 572 may be arranged between and fixedly coupled with actuator wheels 576A and 576B. Wheels 576A and 576B comprise respective engagement elements (e.g., protrusions) 577A and 577B.

In the example shown, the actuator may include one or more pusher elements 578A and 578B which, to retain blocking element 572 in the closed configuration, engage with corresponding protrusion 577A and 577B of actuator wheels 576A and 576B.

Retracting the pusher elements 578A and 578B as schematically shown by arrow P along the pusher elements' longitudinal axes T, causes rotation of blocking element 572 about rotation axis R, as schematically illustrated with arrow M. As a result, front edge 573 does not press against tubing 502, allowing substantially unobstructed flow of fluid through tubing 502, as schematically shown in FIGS. 8G and 8H.

Figure 8I:
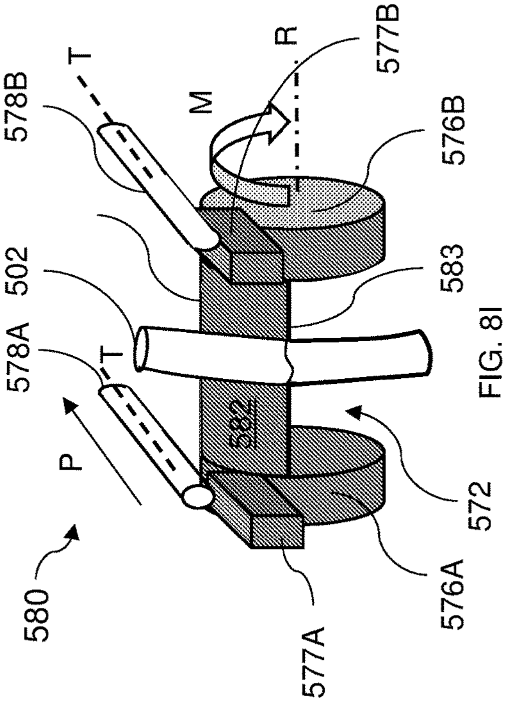
FIG. 8I is a schematic illustration of a flow breaker in a blocking configuration, according to some alternative embodiments.
Figure 8K:
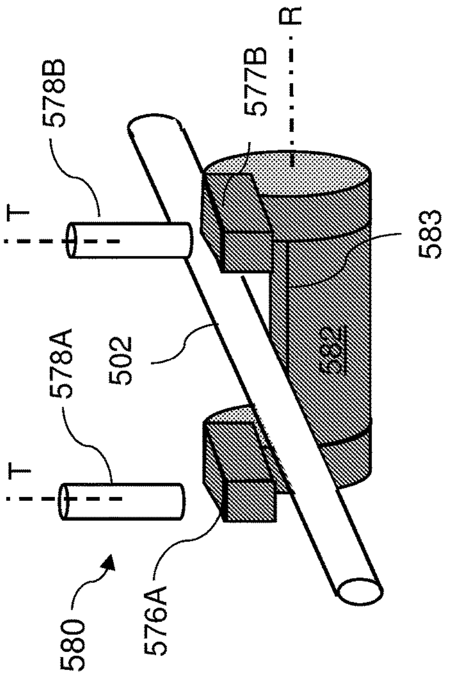
FIGS. 8J and 8K are a schematic illustrations of the flow breaker of FIG. 8I in an open or non-blocking configuration, according to some other embodiments.
Figure 8J:
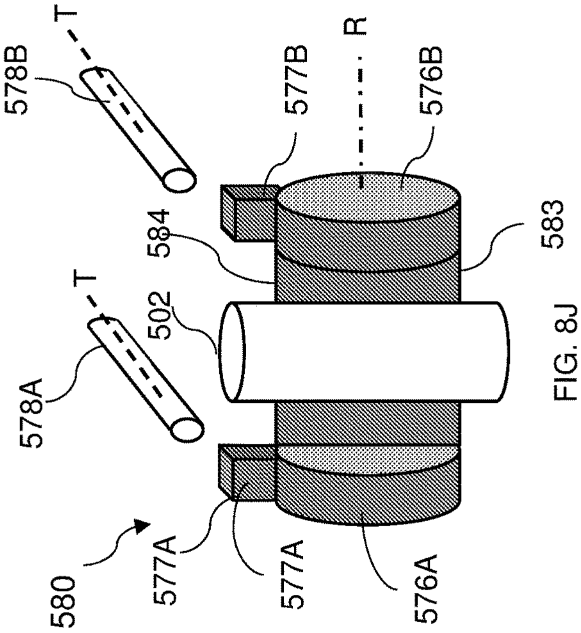

Additional reference is made to FIGS. 8I to 8K. In some embodiments, a rotatable blocking element 580 may be implemented as or comprise a semi-circular body 582 having a front edge 583 and a rear edge 584.

Analogous to what is described with respect to FIGS. 8F to 8H, when blocking element 580 is in the closed configuration (FIG. 8I), front edge 583 applies pressure against tubing 502 causing the obstruction of flow through the tubing. Conversely, when blocking element 580 is in the open configuration (FIGS. 8J and 8K), fluid may flow substantially unobstructed through tubing 502.

Figure 8M:
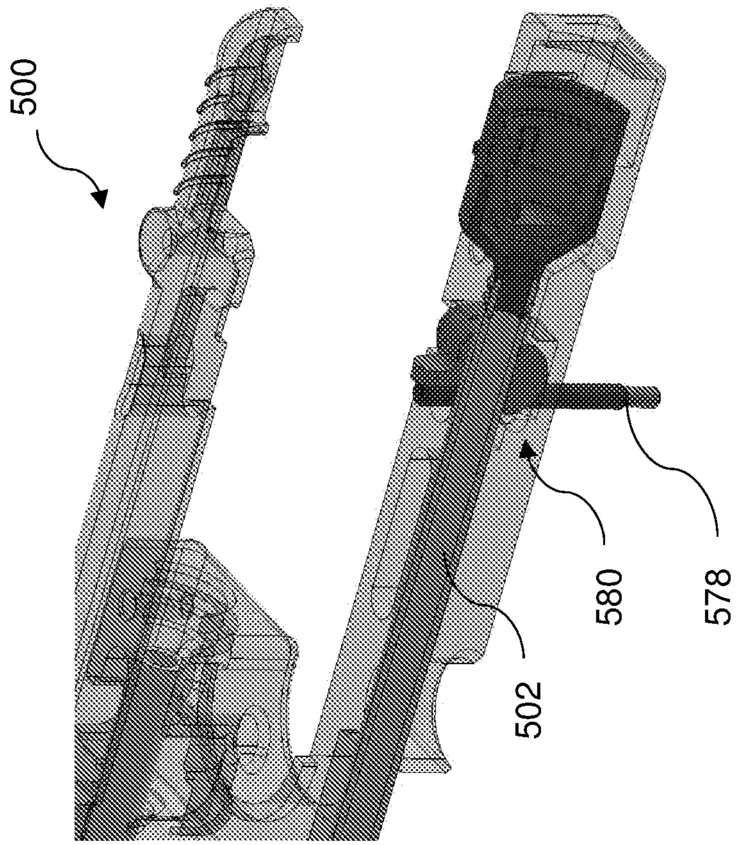
FIG. 8M is a schematic partial view of the disposable cartridge and of the flow breaker of FIG. 8I in the open configuration, according to the alternative embodiment.
Figure 8L:
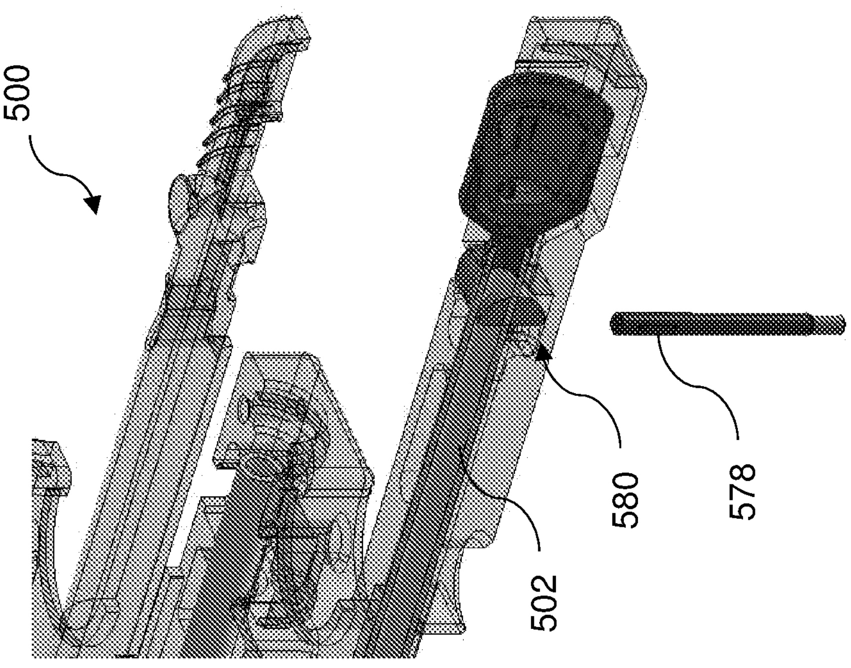
FIG. 8L is a schematic partial view of the disposable cartridge and of the flow breaker of FIG. 8I in the closed configuration, according to the alternative embodiment.

Further reference is made to FIGS. 8L and 8M. FIG. 8L is a schematic partial cutaway illustration of disposable cartridge 500 in which blocking element 580 is in the closed configuration. FIG. 8M is a schematic partial cutaway illustration of disposable cartridge 500 in which blocking element 580 is set in the open configuration.

Figures 9A, 9B, 9C:
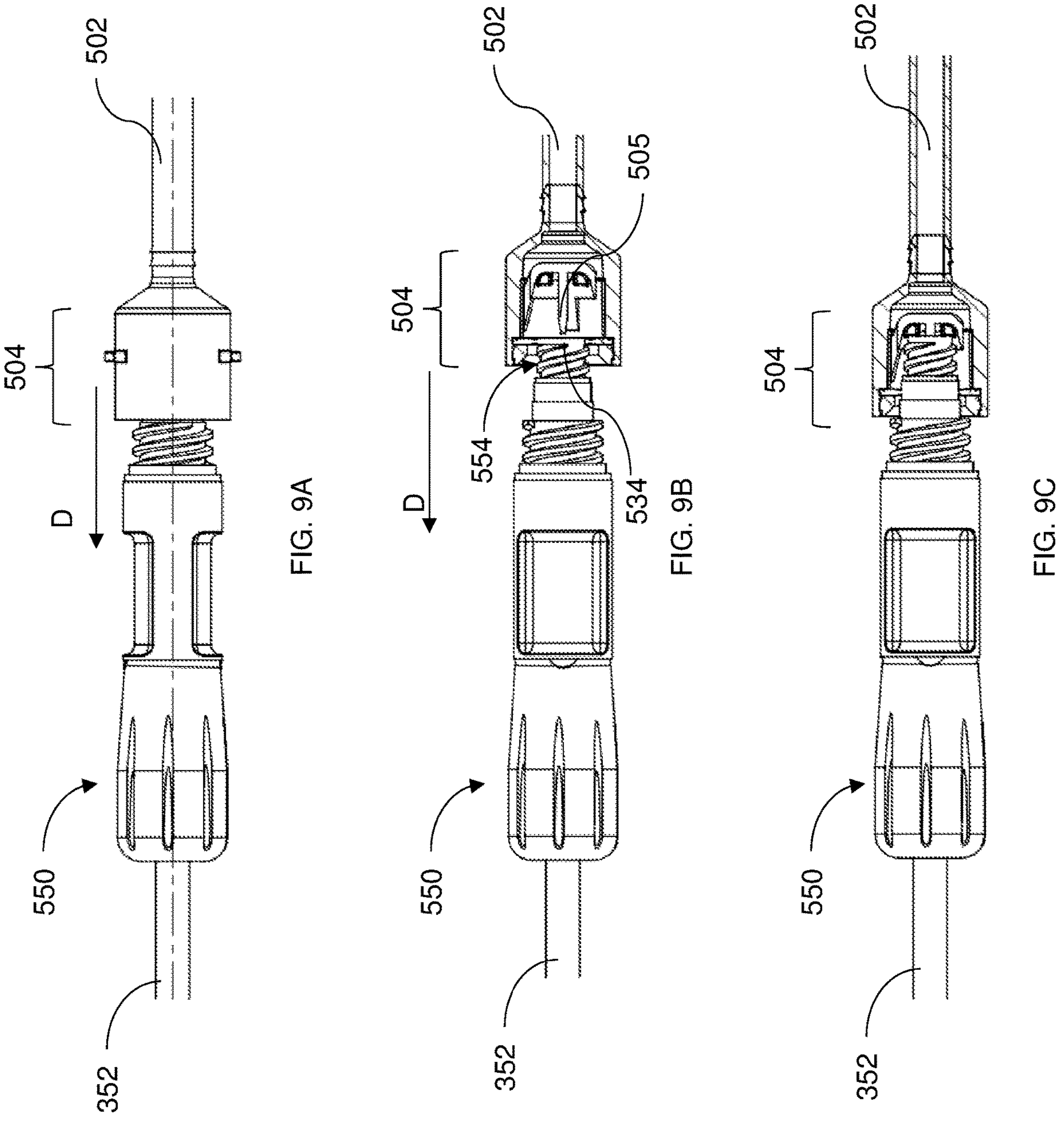
FIGS. 9A to 9C schematically show different assembly views of a patient catheter and external catheter connection, according to some embodiments.

Additional reference is made to FIGS. 9A-9C. As described for example in PCT application WO/2017/134657 filed 1 Feb. 2017 and titled "DIALYSIS SYSTEM PUMP WITH CONNECTOR" to Liberdi Ltd., and in PCT application WO/2018/142406, filed Jan. 2, 2018, titled "SMART PERITONAL DIALYSIS DEVICE" to Liberdi Ltd, both of which are incorporated herein by reference in their entirety, the tubing may include one or more disinfecting lumen or chambers 513 filled with a disinfecting material.

In some embodiments, a catheter-side disinfecting chamber is bounded, for example, by a proximal catheter barrier, and a distal catheter barrier; and a Y-connector disinfection chamber may be bounded, for example, by a proximal Y-connector barrier and a distal Y-connector barrier. A barrier may for example be implemented by a foil or membrane.

A proximal catheter barrier is a barrier that is proximal to patient catheter tubing 352, and a distal catheter barrier is a barrier that is distal to patient catheter tubing 352. A proximal Y-connector barrier may include or is a barrier that is proximal to Y-connector set 560, and a distal Y-connector barrier is a barrier that is distal to Y-connector set 560.

Merely to simplify the discussion that follows, without be construed in a limiting manner, the discussion that follows refers to the catheter-side disinfection chamber.

In some embodiments, catheter connector 504 may include a proximal catheter barrier 534, and a piercing element 505 of a diffuser or piercing device 507 having a proximal opening and a distal opening.

In some embodiments, slider platform is configured to securely (form-fittingly and/frictionally-fittingly) receive external catheters elements, such as catheter tubing 551 and associated external catheter connector 550, and/or Y-tubing 562 and associated external Y-connector 560. Furthermore, disposable part 500 is configured to securely receive (form-fittingly and/frictionally-fittingly) the pump tubing. Once external catheters elements and pump tubing are securely mounted or received by their respective receiving elements of, e.g., slider platform, and the lid 610 and/or base part 602, tube axes and external catheter element axes may be in substantial alignment with each other such that displacement of external catheter elements relative to pump tubing 502 over a certain distance in axial direction of the tubes causes fluid coupling of the external catheter elements with the pump tubing.

In some embodiments, in a same sliding movement slider platform relative to pump tubing 500 traversing over a sufficient distance, the configurations of flow breaker(s) are altered such to bring catheter tubing 551, external Y-tubing 562, and pump tubing 502 in fluid communication with each other.

When causing linear displacement of the external connector 550 and patient connector 504 relative to one another, e.g., by pushing the patient connector 504 against the external connector 550 as schematically shown by arrow D, to obtain a relative displacement from an initial or closed position (FIGS. 9A and 9B) to a second or open position (FIG. 9C), front edge or portion 554 of external connector 550 engages with proximal catheter barrier 534, causing deformation (e.g., stretching) of the proximal catheter barrier 534. Additional relative displacement of the two connectors further results in engagement of the (e.g., stretched) barrier against a piercing element 505 of the connector, and ultimately results in the piercing and/or tearing of the proximal barrier by piercing element 505 such that the external connector 550 and the patient tubing connector 504 become fluidly coupled with each other. This may allow the flow of disinfection fluid out of the disinfection chamber into the patient catheter tubing. Piercing element 505 may be part of a piercing device (also: diffuser).

In some examples, the distal barrier, which may be implemented by a compressed tubing wall, is outlined herein for instance with respect to FIG. 8A, may be decompressed, e.g., through the displacement in direction D, causing unclamping of the tubing by spring elements 806 and 814, allowing disinfecting fluid to flow outside the disinfection chamber, e.g., for example into additional parts of the pump tubing. In some other embodiments, the distal barrier may be a second barrier incorporated in a connector (e.g., catheter tubing connector 504).

Figure 10:
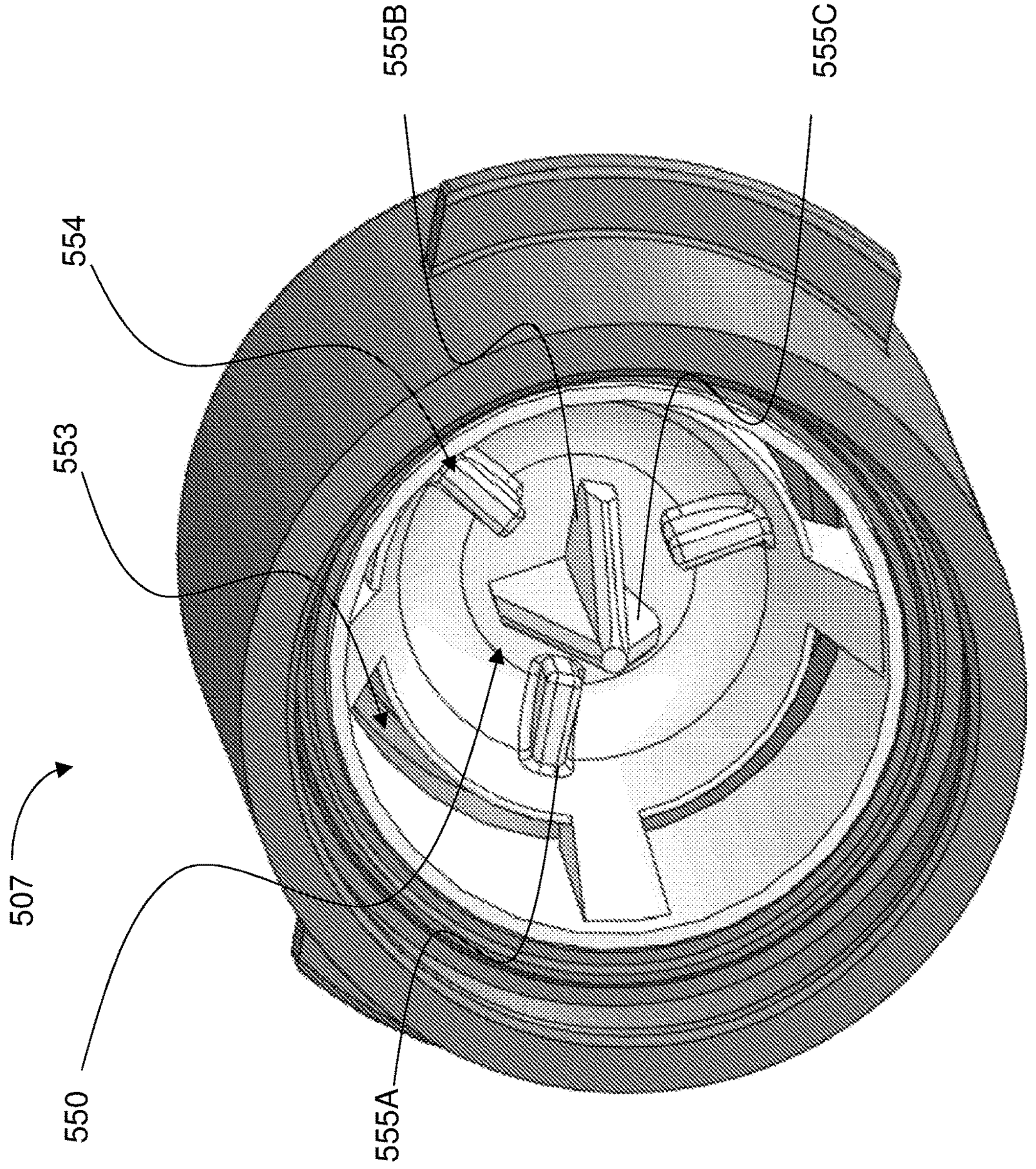
FIG. 10 schematically shows a membrane piercing device, according to some embodiments.

As is shown in FIG. 10, piercing element 505 may be configured to allow, after piercing of the proximal membrane, flow of fluid e.g., from the disinfection chamber into the patient connector tubing or vice versa through openings 553, e.g., of the piercing device. For example, piercing element 505 may have a broadhead shape, formed by a plurality of blades 552 (e.g., blades 552A-C). In some embodiments, piercing device may include one or more spacer elements 555 to prevent sealing of the openings 553 by the front edge or portion 554 of external catheter connector 550.

Figure 11A:
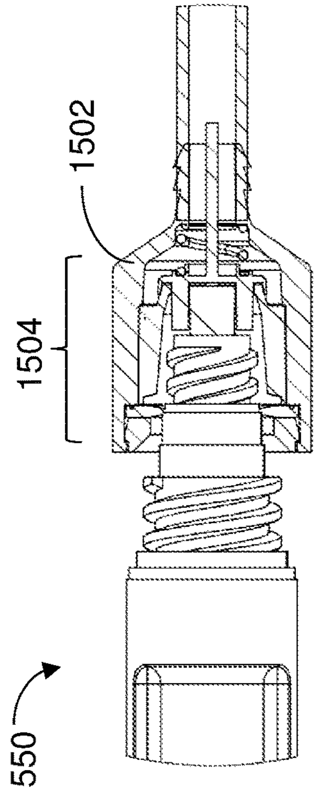
FIGS. 11A-11C schematically show different assembly view of a patient catheter and external catheter connection, according to some other embodiments.
Figure 11B:
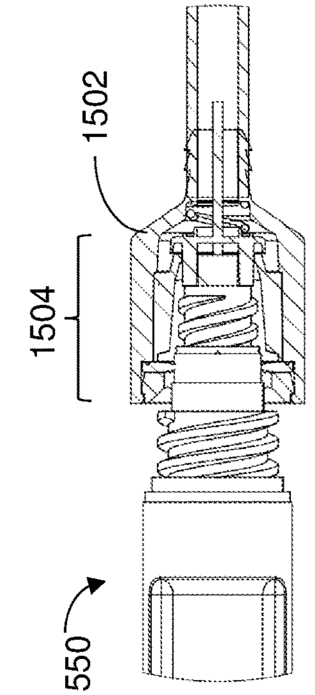
Figure 11C:
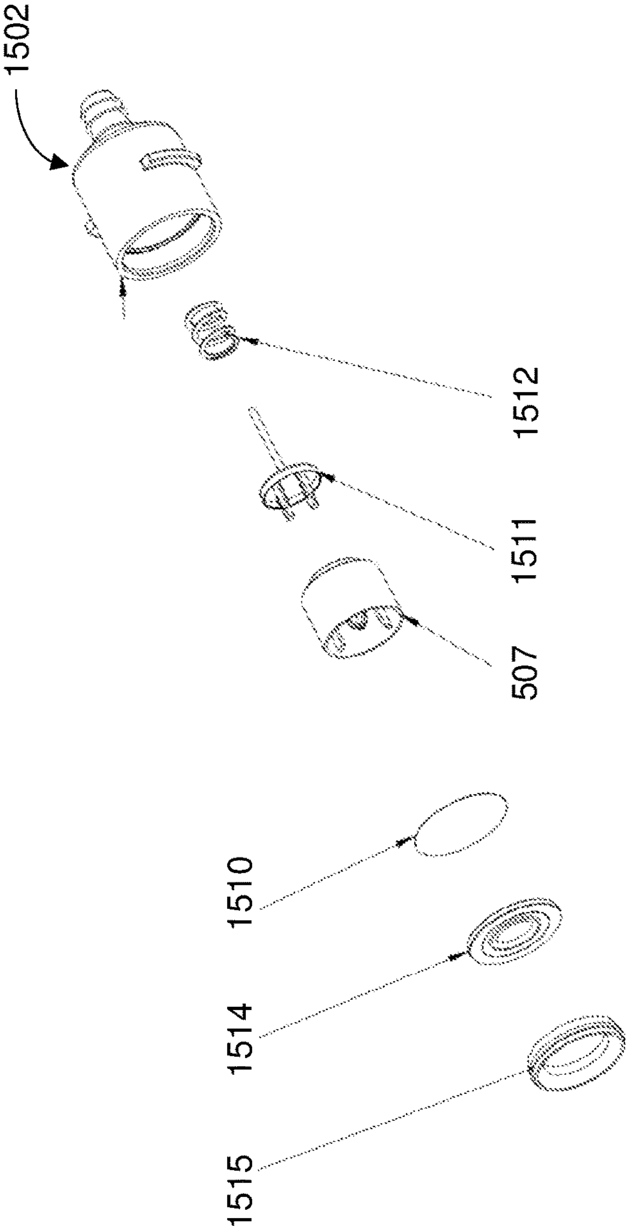

Referring to FIGS. 11A to 11C, one or both connectors such as for example the catheter connector and/or the Y-connector may include a proximal barrier and/or a distal barrier. This way, disinfection material may be exclusively stored within the connector until release of the disinfection material into pump tubing and/or the patient catheter and/or the Y-tubing. Providing such distal barrier (e.g., valve element) that is housed in a connector may obviate the need of employing a mechanical energy storage element such as those shown in FIGS. 8A-8C for clamping onto or compressing onto pump tubing to create the distal barrier.

In some example implementations, each one of the two connectors may include only one barrier, and the disinfection fluid may be stored in tubing 502 between the two barriers. In some examples, a barrier may be considered to be a flow-breaker.

In some example implementations, one of or both connectors may include a proximal and a distal barrier, and the disinfection fluid may be stored within the connectors between their respective two barriers. Here also, each barrier may be considered to be a flow breaker.

In some example implementations, one or both connectors may include a proximal barrier and/or a distal valve configured, for example, as outlined further below. The disinfection fluid may be stored within the proximal barrier and the distal valve. The barrier and the corresponding distal valve may each be considered to be a flow breaker.

Depending on the context, the term "proximal barrier" refers to a barrier or flow breaker position that is closer to the opening of the corresponding connector end.

By implementing a distal barrier with a valve instead of with a mechanical storage element clamping onto the pump tubing may facilitate assembly of the tubing in the cartridge.

It is noted that although the distal barrier is herein shown as being implemented by a valve, this should by no means be construed as limiting. Hence, in some alternative embodiments, the disinfection fluid may be stored in the external connector and, for example, the proximal barrier may be implemented by a valve and the distal barrier may be implemented by valve, and, for example, a foil piercing operation may occur in a direction opposite to the direction D shown in FIGS. 9A-9C. Storing disinfection fluid in the connector only may prolong shelve life due to lower porosity of the connector material compared to the porosity of the tubing material.

In some examples, a biasing element may be embodied by a proximal end of Y-set tubing 506 (proximal to pump rotator 700) and/or of a catheter, which, due to relative displacement to the respective proximal barrier (Y-connector barrier and/or catheter barrier), cause rupturing of the corresponding barrier.

It is noted that although examples schematically illustrated in the accompanying figures and discussed herein relate to embodiments where the disposable part remains static with respect to the durable unit, and the sliding platform and/or a biasing element is controllably displaced relative to durable part and thus, relative to the disposable part, this should by no means be construed as limiting. Accordingly, in some embodiments, the system may be configured such that the disposable part is slidable relative to a biasing element (e.g., a proximal end of y-tubing connector and/or a proximal end of a catheter tubing connector and/or a spring biasing element); or both the disposable part and/or the sliding platform and/or a biasing element may be movable relative to the durable unit. In some or all embodiments, a biasing element may be considered to be the element that contributes to the opening of a flow breaker (e.g., the rupturing of the corresponding barrier and/or the opening of the valve and/or the biasing of the mechanical energy storage device such as flow-breaker spring to an open position).

In some examples, one or both connectors may include a diffuser (e.g., a septum wall) having a plurality of diffusing openings. In the closed configuration, the legs of a valve element may plug the diffusing openings to prevent the flow of fluid through the diffusing openings. In the open configuration, the legs are retracted to allow the flow of fluid through the diffusing openings. FIG. 11A schematically shows a cross-sectional view of a catheter connector 1504 and external connector assembly 550 where the proximal barrier 1510 is torn and a distal barrier or valve element 1511 abuts or is pressed by a mechanical energy storage device (e.g., spring 1512) against the distal opening of a piercing device 507, thereby sealing the piercing device's distal opening. Hence, the disinfection chamber whose cavity is defined by the catheter body and the proximal and distal barrier, is open at the side of the (torn) proximal barrier and closed by the distal (valve-based) barrier 1511.

FIG. 11B schematically shows a cross-sectional view of catheter connector 1504 and external connector assembly 550 where the proximal barrier 1510 is torn and wherein a distal barrier or valve element 1511 is pushed away from the distal opening of piercing device 507 by front end 554 of external connector 550, thereby opening the piercing device's distal opening. Thus configured, both inlets and outlets of catheter connector 1504 are in fluid communication with the external connector and with the pump tubing, allowing the flow of disinfection material through the catheters and tubings.

As is schematically shown in FIG. 11C, a housing of connector 1504 may include a seal 1514 and an adapter 1515. Seal 1514 may be disposed between adapter 1515 and proximal membrane 1510. Furthermore, membrane 1510 may be disposed between sealing element 1514 and the proximal opening of diffuser/piercing device 507. Distal barrier (valve barrier) 1511 may be disposed between mechanical energy storage element 1511 and the distal opening of diffuser 507. It is noted that the Y-tubing connector may be designed in a similar or analogous manner.

Furthermore, in some embodiments, some of the elements shown in FIG. 11C may also be employed in connector embodiments where, for example, the distal barrier is implemented through clamping onto the pump tubing.

Figure 12A:
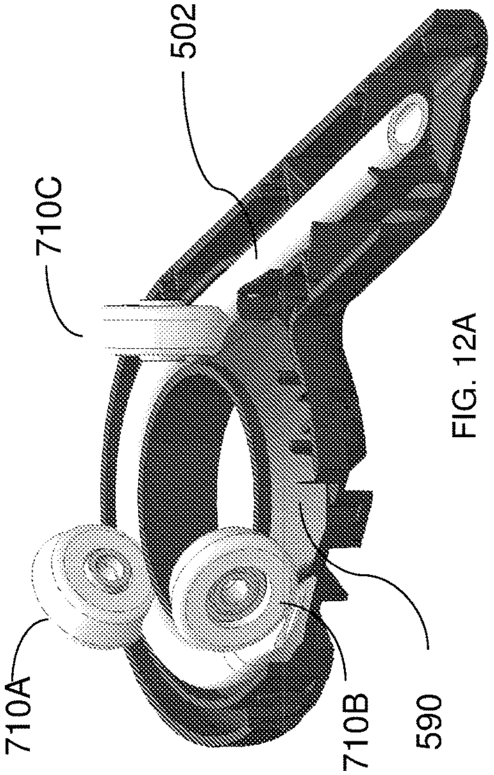
FIGS. 12A and 12B schematically show various views of pump rotor elements engaging with pump tubing, according to some embodiments.
Figure 12B:
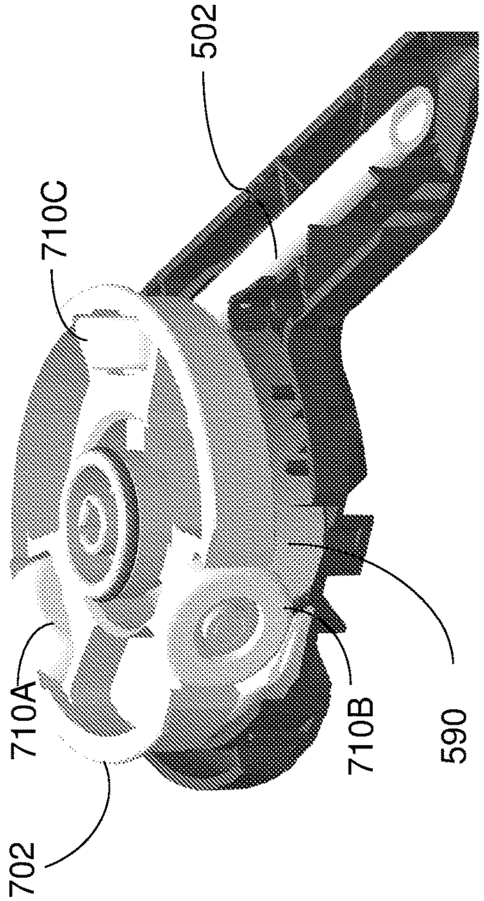

Referring now to FIGS. 12A and 12B, an upper part 514 of the cartridge may include a support structure 590 to support rollers 710 traversing the circular section that does not comprise pump tubing 502. For example, the circular section of the cartridge may be the area in the cartridge defined by a first pump tubing portion from which the wheels, during rotation, disengage and by a second pump tubing portion with which the wheels subsequently reengage. The support structure or platform may be configured, e.g., to reduce or prevent tilting of rotor rotation axis Z relative to the cartridge. In some examples, a wheel engagement surface of support structure 590 has an inclination matching the angle of the tapering rim surfaces of wheels 710A-710C.

It is noted that at least one or all elements schematically illustrated as being included in the upper part of the disposable cartridge may, in some embodiments, be arranged or included in lid 610 instead. For example, at least one fin (e.g., at least one straight fin 529 and/or at least one diagonal fin 532) and/or the support structure 590 may be part of lid 610 instead of being included in the upper part of the disposable cartridge.

Figure 13A:
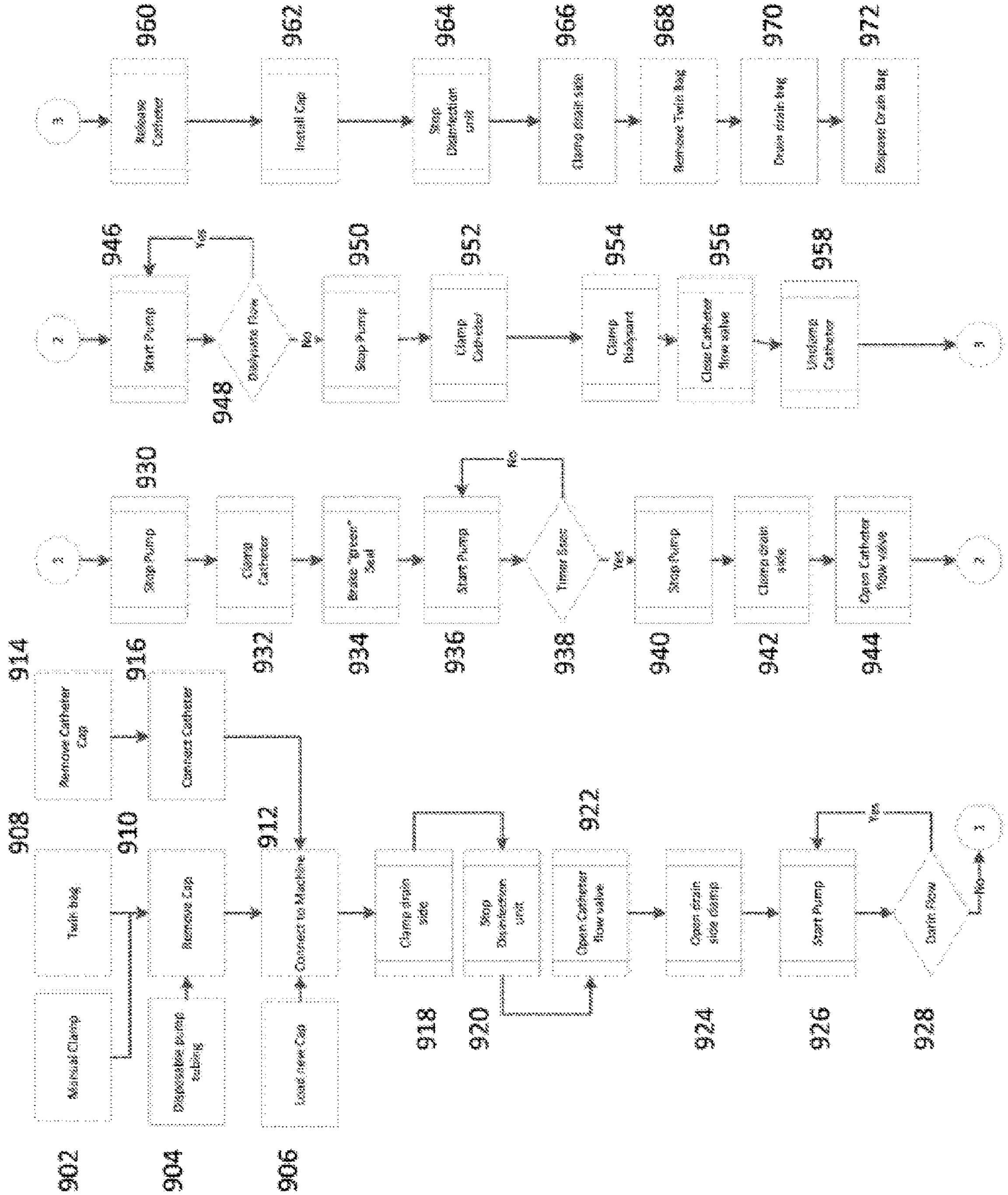
FIGS. 13A and 13B are schematic flow charts of a method for performing peritoneal dialysis, according to some embodiments.

Reference is now made to FIG. 13A. A method for performing peritoneal dialysis, according to some embodiments, may be implemented as set forth herein. According to some embodiments, the cap of a twin bag 908 is removed at 910.

In some embodiments, a manual clamp 902 is added to the twin bag, for example to control the flow into and from the twin bag. Optionally, two clamps are added, one for each bag of the twin bags. In some embodiments, a disposable pump tubing 904 is connected to the twin bag. In some embodiments, the twin bags are connected to the device/system, for example system 300, dialysis device 102 or dialysis device 202. In some embodiments, when the twin bags are connected to the device, a disinfection process initiates, for example to disinfect a flow path between the twin bags and the pump tubing.

According to some embodiments, a catheter cap is removed at 214, and the catheter, for example a catheter of a patient is connected to the device at 916. In some embodiments, during the connection of the catheter a disinfection process initiates, for example to disinfect a flow path between the catheter and the pump tubing. In some embodiments, the drain side of the twin bags is clamped at 918. In some embodiments, the disinfection unit is stopped at 920. In some embodiments, the catheter flow valve is opened at 922. In some embodiments, the drain side claim is opened at 924, for example to allow drained dialysate to enter the draining bag.

According to some embodiments, the pump is activated at 926. In some embodiments, the pump, for example a peristaltic pump rotates a rotor in a direction towards the draining bag. In some embodiments, if drained dialysate flows into the draining bag then the pump remains activated. In some embodiments, if the drained dialysate does not flow, then the pump is stopped at 930.

According to some embodiments, the catheter is clamped at 932. In some embodiments, a seal brakes at 934. In some embodiments, the seal brakes for example, to allow washing of the drained dialysate from the pump tubing. In some embodiments, the pump is activated at 936. In some embodiments, the pump is activated for a desired time period to wash the pump tubing. In some embodiments, when the desired time period is over, the pump is stopped at 940. In some embodiments, the drain side is clamped at 942. In some embodiments, the catheter flow valve is opened at 944, for example to allow a flow path between the fresh dialysate bag and the catheter.

According to some embodiments, the pump is activated at 946. In some embodiments, the pump remains activated as long as dialysate flows into the catheter. In some embodiments, if dialysate does not flow, then the pump is stopped at 950. In some embodiments, the catheter is clamped at 952, for example to isolate the catheter from the pump tubing. In some embodiments, the dialysate is clamped at 954. In some embodiments, the catheter flow valve is closed at 956, for example to prevent any flow into and out from the catheter.

According to some embodiments, the catheter is undamped at 958. In some embodiments, the catheter is released or disconnected at 960. In some embodiments, a cap is installed on the catheter opening at 962. In some embodiments, the disinfection unit is stopped at 964.

According to some embodiments, the drain side is clamped at 966. In some embodiments, the twin bag is removed at 968. In some embodiments, the drain bag is drained at 970. In some embodiments, the drain bag is disposed at 972.

According to some exemplary embodiments, the disposable pump tubing 904 is also disconnected from the device. In some embodiments, new disposable pump tubing is added to the device between an infusion process and a draining process.

Figure 13B:
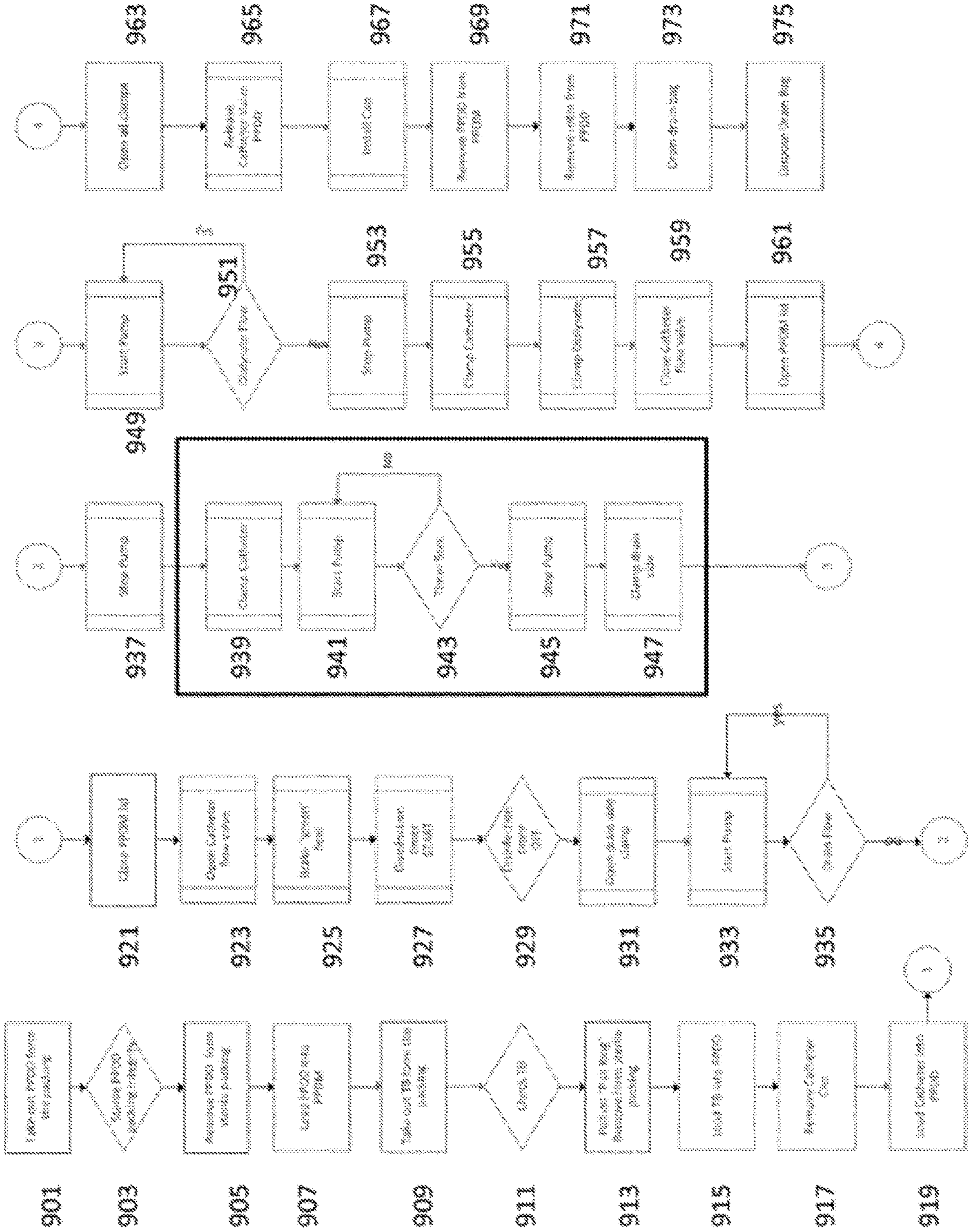

Further reference is now made to FIG. 13B. According to some embodiments, a portable peritoneal dialysis disposables (PPDD) is taken out from a packing at 901. In some embodiments, the sterility of the PPDD packing is examined and/or determined at 903. In some embodiments, the sterility of the packing is determined by examining the integrity of the packing at 903. In some embodiments, if the packing is sterile the PPDD is removed from the packing at 905.

According to some embodiments, the PPDD is loaded into a portable peritoneal dialysis machine (PPDM) at 907. In some embodiments, the PPDM is a durable part of the device, and the PPDD is the disposable part of the device. In some embodiments, the tubing is taken out from the packing, optionally a disposable packing, at 909. In some embodiments, the tubing is examined at 911. In some embodiments, a “pull ring” is removed from the sterile packing at 913. In some embodiments, the tubing is loaded into the PP dialysis disposable. Optionally, the tubing is placed in association with a pump rotor of the PP dialysis disposable.

According to some embodiments, the tubing is loaded into the PP dialysis disposable at 915.

In some embodiments, the catheter cap, for example a patient catheter cap is removed at 917. In some embodiments, the catheter is loaded into the PP dialysis disposable at 919. Optionally, during the loading of the catheter, the catheter is disinfected by a disinfecting connector of the PPDD.

According to some embodiments, the lid of the PP dialysis machine is closed at 921. Optionally, closing the lid initiates a disinfection process of the catheter. In some embodiments, the catheter flow valve is opened at 923. In some embodiments, a seal, for example a “green” seal is broken at 925. Optionally, breaking of the seal releases disinfecting solution into the catheter. In other embodiments, the disinfection process is effected in the manner or one of the manners described above.

According to some embodiments, a disinfection timer is initiated at 927. In some embodiments, the disinfection timer is stopped 929. In some embodiments, the disinfection timer sets a desired time period sufficient for disinfecting a flow path between the tubing and the catheter. In some embodiments, a drain side clamp is opened at 931. In some embodiments, the pump is activated at 933, for example to drain dialysate from the peritoneal cavity. In some embodiments, if fluid is drained at 935 then the pump remains activated. In some embodiments, if there is no fluid to drain, the pump is stopped at 937.

According to some embodiments, the catheter is clamped at 939. In some embodiments, the pump is activated at 941, for example to clear the residual drained dialysate from the tubing. In some embodiments, the pump is activated, optionally by a timer, for at least 2 seconds, for example 2,3,4,5,6,7 seconds or and intermediate or longer time period at 943. Alternatively, the pump is activated until there is no residual fluid in the tubing. In some embodiments, the pump is stopped at 945. In some embodiments, the drain side is clamped at 947.

According to some embodiments, the catheter clamp is released. In some embodiments, the dialysate clamp is released. In some embodiments, the pump is activated at 949, for example to allow infusion of dialysate into the catheter. In some embodiments, dialysate flows into the catheter at 951. In some embodiments, the pump remains activated as long dialysate flows into the catheter. In some embodiments, the pump is stopped 953 when dialysate does not flow into the catheter. Optionally, the pump is stopped following an activation parameter of the treatment protocol. In some embodiments, the catheter is clamped at 955. In some embodiments, the dialysate is clamped at 957. In some embodiments, the catheter flow valve is closed at 959.

According to some embodiments, the PP dialysis machine lid is opened at 961. In some embodiments, all clamps are opened at 963. In some embodiments, the catheter is released from the PP dialysis disposable at 965. In some embodiments, a cap is installed on the catheter opening.

According to some embodiments, the PP dialysis disposable is removed from the PP dialysis machine at 969. In some embodiments, the rotor is removed from the PPDD at 971. In some embodiments, the drain bag is drained at 973. In some embodiments, the drain bag is disposed at 975. Optionally, the PP dialysis disposable or just the tubing is disposed at 975.

ADDITIONAL EXAMPLES

Example 1 pertains to a pump rotor of a pump, wherein the pump rotor is operably couplable with a pump drive of the pump, the pump rotor having a rotor rotation axis Z that is normal to a rotation plane of the pump rotor; the pump rotor comprising at least one wheel that is rotatably coupled with the pump rotor and having a wheel rotation axis W that is perpendicular to from the rotor rotation axis Z; and wherein rotation of the pump rotor about the rotation axis Z causes rotation of the at least one wheel about the wheel rotation axis W such that the at least one wheel traverses a circular path around the rotation axis Z and compresses a corresponding portion of the compressible tube in a direction which is in direction of the pump rotor axis.

Example 2 includes the subject matter of Example 1 and, optionally, wherein rotation of the pump rotor about the rotation axis Z causes wheel rotation axis W to circulate about the rotor rotation axis Z in the rotor rotation plane.

Example 3 includes the subject matter of any one of the preceding examples 1-2, and optionally, wherein the at least one wheel has a rim surface configured to offset for differences in angular velocity when circulating about the rotor rotation axis Z.

Example 4 includes the subject matter of any one or more of the Examples 1 to 3 and, optionally, wherein the at least one wheel has a rim surface tapering towards the rotor rotation axis Z.

Example 5 includes the subject matter of example 4 and, optionally, wherein the rim surface is that of a frustum.

Example 6 includes the subject matter of any one or more of the examples 1 to 5 and, optionally, a shaft configured to operably receive the pump rotor in a pick-and-place assembly step in direction of the rotor rotation axis Z.

Example 7 pertains to a disposable part comprising a compressible tube having a channel for fluid flow wherein when operably assembled with the pump rotor, the compressible tube is sandwiched between the rim surface and the rotor housing.

Example 8 includes the subject matter of Example 7 and, optionally, an actuatable mechanical energy storage element configured to compress the tube to create a disinfection portion comprising disinfecting material.

Example 9 includes the subject matter of example 8 and, optionally, wherein the actuatable mechanical energy storage element is reversibly or non-reversible configurable from a closed configuration to an open configuration.

Example 10 includes the subject matter of Example 8 and/or Example 9 and, optionally, wherein the actuatable mechanical energy storage element is reversibly or non-reversible configurable from an open configuration to a closed configuration.

Example 11 includes the subject matter of any one or more of the Examples 8 to 10, and optionally, wherein the actuatable mechanical energy storage element is a spring that compresses the tube to create a disinfection portion comprising disinfecting material.

Example 12 includes the subject matter of any one or more of Examples 7 to 11 and, optionally, wherein relative motion is controllably initiatable between the spring and a biasing element which causes release of the pressure applied onto the tube by the spring, thereby allowing flow of the disinfection material into the tube.

Example 13 includes the subject matter of example 11 and/or example 12 and, optionally, wherein the spring is normally closed, having a closed state whereby a part of the spring presses onto tube of disposable part.

Example 14 includes the subject matter of any one or more of the Examples 7 to 13, wherein the disposable part operably engageable with a pump rotor of a peritoneal dialysis device, e.g., as disclosed herein.

Example 15 includes the subject matter of example 14 and, optionally, wherein the pump rotor is part of a durable unit of the peritoneal dialysis device. In some examples, the pump rotor may be a durable pump rotor.

In some examples, the actuatable mechanical energy storage element and/or the actuator may be part of the durable unit.

While the invention has been described with respect to a limited number of embodiments, it will be appreciated that many variations, modifications and other applications of the invention may be made. Therefore, the claimed invention as recited in the claims that follow is not limited to the embodiments described herein.

It is important to note that the methods described herein and illustrated in the accompanying diagrams shall not be construed in a limiting manner. For example, methods described herein may include additional or even fewer processes or operations in comparison to what is described herein and/or illustrated in the diagrams. In addition, method steps are not necessarily limited to the chronological order as illustrated and described herein.

Any digital computer system, unit, device, module and/or engine exemplified herein can be configured or otherwise programmed to implement a method disclosed herein, and to the extent that the system, module and/or engine is configured to implement such a method, it is within the scope and spirit of the disclosure. Once the system, module and/or engine are programmed to perform particular functions pursuant to computer readable and executable instructions from program software that implements a method disclosed herein, it in effect becomes a special purpose computer particular to embodiments of the method disclosed herein. The methods and/or processes disclosed herein may be implemented as a computer program product that may be tangibly embodied in an information carrier including, for example, in a non-transitory tangible computer-readable and/or non-transitory tangible machine-readable storage device. The computer program product may directly loadable into an internal memory of a digital computer, comprising software code portions for performing the methods and/or processes as disclosed herein.

The methods and/or processes disclosed herein may be implemented as a computer program that may be intangibly embodied by a computer readable signal medium. A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a non-transitory computer or machine-readable storage device and that can communicate, propagate, or transport a program for use by or in connection with apparatuses, systems, platforms, methods, operations and/or processes discussed herein.

The terms “non-transitory computer-readable storage device” and “non-transitory machine-readable storage device” encompasses distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by one or more communication networks.

These computer readable and executable instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable and executable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable and executable instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The term “engine” may comprise one or more computer modules, wherein a module may be a self-contained hardware and/or software component that interfaces with a larger system. A module may comprise a machine or machines executable instructions. A module may be embodied by a circuit or circuitry, or a controller programmed to cause the system to implement the method, process and/or operation as disclosed herein. For example, a module may be implemented as a hardware circuit comprising, e.g., custom VLSI circuits or gate arrays, an Application-specific integrated circuit (ASIC), off-the-shelf semiconductors such as logic chips, transistors, and/or other discrete components. A module may also be implemented in programmable hardware devices such as field programmable gate arrays, programmable array logic, programmable logic devices and/or the like.

The term “random” also encompasses the meaning of the term “substantially randomly” or “pseudo-randomly”.

The expression “real-time” as used herein generally refers to the updating of information based on received data, at essentially the same rate as the data is received, for instance, without user-noticeable judder, latency or lag.

In the discussion, unless otherwise stated, adjectives such as “substantially” and “about” that modify a condition or relationship characteristic of a feature or features of an embodiment of the invention, are to be understood to mean that the condition or characteristic is defined to within tolerances that are acceptable for operation of the embodiment for an application for which it is intended.

Unless otherwise specified, the terms “substantially”, “about” and/or “close” with respect to a magnitude or a numerical value may imply to be within an inclusive range of −10% to +10% of the respective magnitude or value.

“Coupled with” can mean indirectly or directly “coupled with”.

It is important to note that the method may include is not limited to those diagrams or to the corresponding descriptions. For example, the method may include additional or even fewer processes or operations in comparison to what is described in the figures. In addition, embodiments of the method are not necessarily limited to the chronological order as illustrated and described herein.

Discussions herein utilizing terms such as, for example, “processing”, “computing”, “calculating”, “determining”, “establishing”, “analyzing”, “checking”, “estimating”, “deriving”, “selecting”, “inferring” or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes. The term determining may, where applicable, also refer to “heuristically determining”.

It should be noted that where an embodiment refers to a condition of “above a threshold”, this should not be construed as excluding an embodiment referring to a condition of “equal or above a threshold”. Analogously, where an embodiment refers to a condition “below a threshold”, this should not be construed as excluding an embodiment referring to a condition “equal or below a threshold”. It is clear that should a condition be interpreted as being fulfilled if the value of a given parameter is above a threshold, then the same condition is considered as not being fulfilled if the value of the given parameter is equal or below the given threshold. Conversely, should a condition be interpreted as being fulfilled if the value of a given parameter is equal or above a threshold, then the same condition is considered as not being fulfilled if the value of the given parameter is below (and only below) the given threshold.

It should be understood that where the claims or specification refer to “a” or “an” element and/or feature, such reference is not to be construed as there being only one of that element. Hence, reference to “an element” or “at least one element” for instance may also encompass “one or more elements”.

Terms used in the singular shall also include the plural, except where expressly otherwise stated or where the context otherwise requires.

In the description and claims of the present application, each of the verbs, “comprise” “include” and “have”, and conjugates thereof, are used to indicate that the data portion or data portions of the verb are not necessarily a complete listing of components, elements or parts of the subject or subjects of the verb.

Unless otherwise stated, the use of the expression “and/or” between the last two members of a list of options for selection indicates that a selection of one or more of the listed options is appropriate and may be made. Further, the use of the expression “and/or” may be used interchangeably with the expressions "at least one of the following", "any one of the following" or "one or more of the following", followed by a listing of the various options.

As used herein, the phrase "A,B,C, or any combination of the aforesaid" should be interpreted as meaning all of the following: (i) A or B or C or any combination of A, B, and C, (ii) at least one of A, B, and C; (iii) A, and/or B and/or C, and (iv) A, B and/or C. Where appropriate, the phrase A, B and/or C can be interpreted as meaning A, B or C. The phrase A, B or C should be interpreted as meaning "selected from the group consisting of A, B and C". This concept is illustrated for three elements (i.e., A,B,C), but extends to fewer and greater numbers of elements (e.g., A, B, C, D, etc.).

It is appreciated that certain features of the invention, which are, for clarity, described in the context of separate embodiments or example, may also be provided in combination in a single embodiment. Conversely, various features of the invention, which are, for brevity, described in the context of a single embodiment, example and/or option, may also be provided separately or in any suitable sub-combination or as suitable in any other described embodiment, example or option of the invention. Certain features described in the context of various embodiments, examples and/or optional implementation are not to be considered essential features of those embodiments, unless the embodiment, example and/or optional implementation is inoperative without those elements.

It is noted that the terms "in some embodiments", "according to some embodiments", "for example", "e.g.,", "for instance" and "optionally" may herein be used interchangeably.

The number of elements shown in the Figures should by no means be construed as limiting and is for illustrative purposes only.

"Real-time" as used herein generally refers to the updating of information at essentially the same rate as the data is received. More specifically, in the context of the present invention "real-time" is intended to mean that the image data is acquired, processed, and transmitted from a sensor at a high enough data rate and at a low enough time delay that when the data is displayed, data portions presented and/or displayed in the visualization move smoothly without user-noticeable judder, latency or lag.

It is noted that the terms "operable to" can encompass the meaning of the term "modified or configured to". In other words, a machine "operable to" perform a task can in some embodiments, embrace a mere capability (e.g., "modified") to perform the function and, in some other embodiments, a machine that is actually made (e.g., "configured") to perform the function.

Positional terms such as "upper", "lower" "right", "left", "bottom", "below", "lowered", "low", "top", "above", "elevated", "high", "vertical" and "horizontal" as well as grammatical variations thereof as may be used herein do not necessarily indicate that, for example, a "bottom" component is below a "top" component, or that a component that is "below" is indeed "below" another component or that a component that is "above" is indeed "above" another component as such directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both.

"Coupled with" means indirectly or directly "coupled with".

It should be noted that the term "light" as used herein may refer to electromagnetic radiation of any suitable wavelength for the purposes of the applications disclosed herein. Accordingly, the term "light" should not be construed as being limited to visible light and may additionally or alternatively include non-visible radiation such as, for example, laser light in the infrared range and UV light.

Accordingly, the term "light" should not be construed as being limited to visible light and may additionally or alternatively include non-visible radiation such as, for example, light in the infrared range, light in the short wave infrared range and light in the ultra-violate range. The light may be coherent, non-coherent or partially coherent. The light may be polarized, non-polarized or partially polarized. The light may have a wide spectral width (e.g., of the range of hundreds of nanometers such as originated from a black body), the light may have a mid-spectral width (e.g., of the range of tens of nanometers such as originated from a LED) or the light may have a narrow spectral width (e.g., of the range of a few nanometers such as originated from a laser). Moreover, the terms "light" and "EM radiation" may herein be used interchangeably.

Throughout this application, various embodiments may be presented in and/or relate to a range format. It should be understood that the description in range format is merely for convenience and brevity and should not be construed as an inflexible limitation on the scope of the embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

While the invention has been described with respect to a limited number of embodiments, these should not be construed as limitations on the scope of the invention, but rather as exemplifications of some of the embodiments.

What is claimed is:

1. A peritoneal dialysis system, comprising:

a controller;

a durable unit, a disposable unit that comprises a housing and that is removably couplable with the durable unit, the disposable unit configured to receive a tube having a channel, the tube being compressible by a wheel of a pump such to cause flow of fluid within the channel;

wherein said disposable unit and/or said tube comprises at least one flow breaker configured to block the flow of fluid through the tube; and wherein the durable unit further comprises a slider platform for receiving at least one biasing element;

at least one actuator controllable by the controller;

wherein the slider platform can be actuated by the at least one actuator to controllably slide, relative to the at least one flow breaker, from a retracted position to an advanced position in a sliding direction (SD) that lies in a sliding plane (SP) which is about parallel to a tubing plane delineated by a fluid flow path defined by the tube;

wherein sliding of the slider platform from the retracted position to the advanced position causes the at least one biasing element to change a flow breaker configuration of the at least one flow breaker from a closed configuration into an open configuration for allowing the flow of fluid through the tube.

2. The dialysis system of 1, wherein the at least one flow breaker is reversibly or non-reversibly configurable from the closed configuration to the open configuration.

3. The dialysis system of claim 1, wherein the at least one flow breaker is reversibly or non-reversibly configurable from the open configuration to the closed configuration.

4. The dialysis system of claim 1, wherein the at least one flow breaker is a barrier and/or a valve incorporated in the tube.

5. The dialysis system of claim 1, wherein the at least one flow breaker is an actuatable mechanical energy storage element.

6. The dialysis system of claim 1, wherein the at least one flow breaker is a rotatable blocking element that is rotatable from the closed position to the open position, enabling substantially unobstructed flow of fluid through the tube.

7. The dialysis system of claim 1, wherein the disposable unit comprises a Y-connector end and a catheter end which are both open in a same direction;

wherein the system is configured to cause relative displacement between the slider platform and the at least one flow breaker actuate relative displacement between the at least one flow breaker and the biasing element to cause the at least one flow breaker to change from the closed configuration to the open configuration for allowing the flow of fluid through the tube.

8. The dialysis system of claim 7, wherein the slider platform includes elevations relative to a base which are shaped and sized to accommodate a Y-set tubing for connecting a Y-set tubing end with the Y-connector of the tubing accommodated by the disposable unit.

9. The dialysis system of claim 1, further comprising a pump drive which is part of the durable unit.

10. The dialysis system of claim 1 further comprising a controller configured to control a dialysis treatment process.

11. The dialysis system of claim 1, further comprising a pump rotor, wherein the pump rotor is operably couplable with a pump drive of the pump, the pump rotor having a rotor rotation axis (Z) that is normal to a rotation plane of the pump rotor;

the pump rotor comprising at least one wheel that is rotatably coupled with the pump rotor and having a wheel rotation axis (W) that is perpendicular to from the rotor rotation axis (Z); and wherein rotation of the pump rotor about the rotation axis (Z) causes rotation of the at least one wheel about the wheel rotation axis (W) such that the at least one wheel traverses a circular path around the rotation axis (Z) and compresses a corresponding portion of the tube.

12. The dialysis system of claim 11, wherein the pump rotor is configured to be operably receivable by a shaft of the pump in a pick-and-place assembly step in a direction of the rotor rotation axis (Z).

13. The dialysis system of claim 11, wherein an upper part of the disposable unit includes a support structure to support the at least one wheel traversing a circular section which is lacking the tube.

14. A peritoneal dialysis system, comprising:

a controller;

a durable unit configured to receive at least one biasing element, a disposable unit that comprises a housing and that is removably couplable with the durable unit, the disposable unit configured to receive a tube having a channel, the tube being compressible by a wheel of a pump to cause flow of fluid within the channel;

wherein the tube and/or the disposable unit comprise at least one flow breaker configured to block the flow of fluid through the tube; and at least one actuator controllable by the controller; wherein the at least one flow breaker and/or the at least one biasing element can be actuated by the at least one actuator to cause controllable sliding of the at least one flow breaker and/or the at least one biasing element relative to each other to change a configuration of the at least one flow breaker from a closed configuration into an open configuration to allow the flow of fluid through the tube.

15. The dialysis system of 14, wherein the at least one flow breaker is reversibly or non-reversibly configurable from the closed configuration to the open configuration.

16. The dialysis system of claim 14, wherein the at least one flow breaker is reversibly or non-reversibly configurable from the open configuration to the closed configuration.

17. The dialysis system of claim 14, wherein the at least one flow breaker is a rotatable blocking element that is rotatable from the closed position to the open position, enabling substantially unobstructed flow of fluid through the tube.

18. The dialysis system of claim 14, wherein the disposable unit comprises a Y-connector end and a catheter end which are both open in a same direction; wherein the system is configured to cause relative displacement between the at least one biasing element and the at least one flow breaker to cause the at least one flow breaker to change from a closed configuration to an open configuration for allowing the flow of fluid through the tube.

19. The dialysis system of claim 1, further comprising a pump drive which is part of the durable unit.

20. The dialysis system of claim 1, further comprising a controller configured to control a dialysis treatment process.

* * * * *